United States Patent

Kohl

[11] Patent Number: 5,773,451
[45] Date of Patent: Jun. 30, 1998

[54] SUBSTITUTED ARYLTHIOALKYLTHIOPYRIDINES

[75] Inventor: Bernhard Kohl, Constance, Germany

[73] Assignee: BYK Gulden Lomberg Chemische Fabrik GmbH, Constance, Germany

[21] Appl. No.: 564,285

[22] PCT Filed: Jun. 28, 1994

[86] PCT No.: PCT/EP95/02098

§ 371 Date: Dec. 20, 1995

§ 102(e) Date: Dec. 20, 1995

[87] PCT Pub. No.: WO95/01351

PCT Pub. Date: Jan. 12, 1995

[30] Foreign Application Priority Data

Jun. 29, 1993 [CH] Switzerland .................. 1995/93

[51] Int. Cl.$^6$ .................. C07D 401/12; A61K 31/04
[52] U.S. Cl. .................. 514/338; 514/269; 514/274; 546/273.7; 546/272.1; 546/271.7; 546/271.1; 546/269.7; 546/272.4; 546/269.1; 546/268.7; 546/256; 544/315; 544/319
[58] Field of Search .................. 546/273.7, 272.1, 546/271.7, 271.1, 269.7, 272.4, 269.1, 268.7, 256; 544/315, 319; 514/338, 269, 274

[56] References Cited

U.S. PATENT DOCUMENTS 4,560,693 12/1985 Rainer .................. 514/338

*Primary Examiner*—Jane Fan
*Attorney, Agent, or Firm*—Jacobson, Price, Holman & Stern, PLLC

[57] ABSTRACT

Described are compounds of formula (I) in which R1,R2, R3,R4,R5,R6,R7, m,n,p, and q are as defined in the description. Such compounds are suitable for use against Helicobacter bacteria.

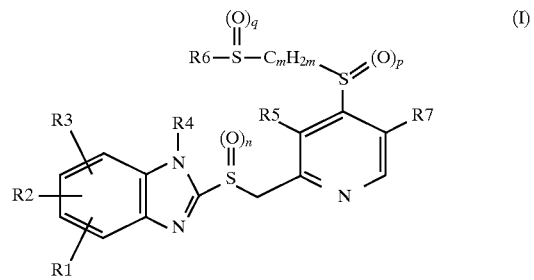

16 Claims, 1 Drawing Sheet

(I)

(II)

(III)

(IV)

SUBSTITUTED ARYLTHIOALKYLTHIOPYRIDINES

FIELD OF USE OF THE INVENTION

The invention relates to compounds which are to be used in the pharmaceutical industry as active compounds for the preparation of medicaments.

KNOWN TECHNICAL BACKGROUND

European Patent Application 150 586 discloses 2-(pyridylmethylthio- and -sulfinyl)benzimidazoles which can be substituted in the 4-position of the pyridine part of the molecule by, inter alia, alkylthio or arylthio radicals. A long-lasting inhibition of the secretion of gastric acid is reported for the compounds described. International Patent Application WO89/03830 states that the same compounds and other structurally similar compounds are suitable for treatment of osteoporosis. International Patent Application WO92/12976 describes 2-(pyridylmethylthio- and -sulfinyl) benzimidazoles which are substituted in a particular manner and are said to be active against Helicobacter bacteria and for which it is furthermore disclosed that they are said to be suitable for the prevention and treatment of a whole range of diseases of the stomach.

SUMMARY OF THE INVENTION

The invention relates to compounds of formula I (see FIG. 1A), in which

R1 is hydrogen, 1-4C-alkyl or 1-4C-alkoxy,

R2 is hydrogen, 1-4C-alkyl, 1-4C-alkoxy, halogen, trifluoromethyl, 1-4C-alkoxy which is completely or predominantly substituted by fluorine, or chlorodifluoromethoxy or 2-chloro-1,1,2-trifluoroethoxy, or, together with R3, is 1-2C-alkylenedioxy which, if desired, is completely or partly substituted by fluorine, or chlorotrifluoroethylenedioxy, R3 is hydrogen, 1-4C-alkoxy which is completely or predominantly substituted by fluorine, or chlorodifluoromethoxy or 2-chloro-1,1,2-trifluoroethoxy or, together with R2, is 1-2C-alkylenedioxy which, if desired, is completely or partly substituted by fluorine, or chlorotrifluoroethylenedioxy, R4 is hydrogen or 1-4C-alkyl, R5 is hydrogen, 1-4C-alkyl or 1-4C-alkoxy, R6 is a cyclic or bicyclic radical which is substituted by R8 and R9 and is chosen from the group consisting of benzene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine N-oxide, pyrimidine and benzimidazole, R7 is hydrogen, 1-4C-alkyl or 1-4C-alkoxy, R8 is hydrogen, 1-4C-alkyl, hydroxyl, 1-4C-alkoxy, halogen, nitro, carboxyl, 1-4C-alkoxycarbonyl, guanidino, 1-4C-alkyl which is substituted by R10, or —N(R11)R12, R9 is hydrogen, 1-4C-alkyl, 1-4C-alkoxy, fluorine or trifluoromethyl, R10 is hydroxyl, 1-4C-alkoxy, carboxyl, 1-4C-alkoxycarbonyl or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino or morpholino radical, R13 is hydrogen, 1-4C-alkyl or 1-4C-alkoxy, m is a number from 2 to 7, n is the number 0 or 1, p is the number 0 or 1 and q is the number 0 or 1, and their salts.

BRIEF DESCRIPTION OF THE DRAWINGS

FIG. 1A is the formula of final products, whereas

Figure 1A:
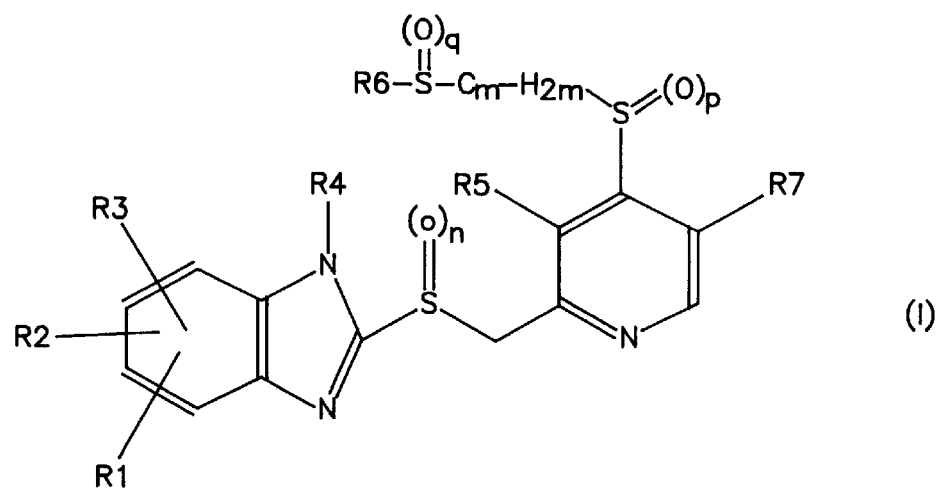

DETAILS 1-4C-alkyl is a straight-chain or branched alkyl radical having 1 to 4 carbon atoms. Examples which may be mentioned are the butyl, isobutyl, sec-butyl, tert-butyl, propyl, isopropyl, ethyl and methyl radicals.

1-4C-alkoxy is a radical which contains one of the above-mentioned 1-4C-alkyl radicals, in addition to the oxygen atom. Examples which may be mentioned are the methoxy and the ethoxy radicals.

Halogen in the context of the present invention is bromine, chlorine and fluorine.

Examples which may be mentioned of 1-4C-alkoxy which is completely or predominantly substituted by fluorine are the 1,2,2-trifluoroethoxy, the 2,2,3,3,3-pentafluoropropoxy, the perfluoroethoxy and, in particular, the 1,1,2,2-tetrafluoroethoxy, the trifluoromethoxy, the 2,2,2-trifluoroethoxy and the difluoromethoxy radicals.

Examples which may be mentioned of 1-2C-alkylenedioxy which, if desired, is completely or partly substituted by fluorine are the methylenedioxy (—O—CH$_2$—O—), the ethylenedioxy (—O—CH$_2$—CH$_2$—O—), the 1,1-difluoroethylenedioxy (—O—CF$_2$—CH$_2$—O—), the 1,1,2,2-tetrafluoroethylenedioxy (—O—CF$_2$—CF$_2$—O—) and, in particular, the difluoromethylenedioxy (O—CF$_2$—O—) and the 1,1,2-trifluoroethylenedioxy (—O—CF$_2$—CHF—O—) radicals.

If R2 and R3 together are 1-2C-alkylenedioxy which, if desired, is completely or partly substituted by fluorine, or chlorotrifluoroethylenedioxy, the substituents R2 and R3 are bonded to the benzo part of the benzimidazole ring in adjacent positions—preferably to positions 5 and 6.

The group —S(O)q— is bonded to a carbon atom of the cyclic or bicyclic radical R6 in question, so that examples of radicals R6 which may be mentioned are the radicals: phenyl, 2-furyl, 3-furyl, 2-thienyl, 3-thienyl, 3-pyrrolyl, 2-oxazolyl, 4-oxazolyl, 4-isoxazolyl, 5-isoxazolyl, 2-thiazolyl, 3-isothiazolyl, 2-imidazolyl, 3-pyrazolyl, 4-pyrazolyl, 1,2,3-triazol-4-yl, 1,2,5-thiadiazol-4-yl, 1,2,4-triazol-3-yl, tetrazol-5-yl, 1,3,4-thiadiazol-2-yl, 1,2,3-thiadiazol-4-yl, 1,3,4-oxadiazol-2-yl, 2-pyridyl, 4-pyridyl, 2-pyrimidinyl and 2-benzimidazolyl.

The substituents R8 and optionally R9 can be bonded to the cyclic or bicyclic radicals R6 at any conceivable position. Examples of substituted radicals R6 which may be mentioned are: 4-methylphenyl, 3-dimethylaminomethylphenyl, 3-piperidinomethylphenyl, 3-carboxymethylphenyl, 2-dimethylaminomethyl-5-methyl-3-furyl, 1-methylpyrrol-3-yl, 4,5-dimethyl-oxazol-2-yl, 3,5-dimethyl-isoxazol-4-yl, 4,5-dimethyl-thiazol-2-yl, 4-methyl-5-carboxymethyl-thiazol-2-yl, 1-methyl-imidazol-2-yl, 1-methyl-pyrazol-3-yl, 1-(2-dimethylaminoethyl)-pyrazol-3-yl, 5-methyl-1,3,4-oxadiazol-2-yl, 1-methyl-1,2,3-triazol-4-yl, 1-methyl-1,2,4-triazol-3-yl, 1-(2- dimethylaminoethyl)-1,2,3-triazol-4-yl, 1-methyl-tetrazol-5-yl, 1-(2-dimethylaminoethyl)-tetrazol-5-yl, 1-carboxymethyl-tetrazol-5-yl, 5-methyl-1,3,4-thiadiazol-2-yl, 5-trifluoromethyl-1,3,4-thiadiazol-2-yl, 1-(2-hydroxyethyl)-tetrazol-5-yl, 2-amino-1,3,4-thiadiazol-2-yl, 3-amino-1,2,4-triazol-5-yl, 4-methyl-5-trifluoromethyl-1,2,4-triazol-3-yl and 4-amino-pyrimidin-2-yl.

Possible radicals —$C_mH_{2m}$— which are substituted by R6-S(O)$_q$— are straight-chain or branched radicals. Examples which may be mentioned are the heptyl, isoheptyl (2-methylhexyl), hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl and ethyl radicals. Examples of radicals R6-S(O)$_q$-$C_mH_{2m}$ which may be mentioned are: phenylthiopentyl, phenylthioethyl, phenylthiopropyl, phenylthiobutyl, 4-methyl-phenylthioethyl, 4-methyl-phenylthiopropyl, 3-dimethylaminomethyl-phenyl-thioethyl, 3-dimethylaminomethyl-phenylthiopropyl, 3-piperidinomethyl-phenylthioethyl, 3-piperidinomethyl-phenylthiopropyl, 3-piperidinomethyl-phenylthiobutyl, 1-methylpyrrole-3-thioethyl, 4,5-dimethyloxazole-2-thiopropyl, 3,5-dimethyl-isoxazole-5-thioethyl, 3,5-dimethyl-isoxazole-5-thiopropyl, thiazole-2-thioethyl, thiazole-2-thiopropyl, thiazole-2-thiobutyl, 4-methyl-5-carboxymethyl-thiazole-2-thiopropyl, 1-methylimidazole-2-thioethyl, 1-methylimidazole-2-thiopropyl, 1-methylimidazole-2-thiobutyl, imidazole-2-thioethyl, imidazole-2-thiopropyl, pyrazole-3-thiopropyl, 1-(2-dimethylaminoethyl)-pyrazole-2-thioethyl, 1,3,4-oxadiazole-2-thioethyl, 1,3,4-oxadiazole-2-thiopropyl, 1,2,3-triazole-4-thioethyl, 1,2,3-triazole-4-thiopropyl, 1,2,3-triazole-thiobutyl, 1-methyl-1,2,3-triazole-4-thioethyl, 1-methyl-1,2,3-triazole-4-thiopropyl, 1,2,4-triazole-3-thioethyl, 1,2,4-triazole-3-thiopropyl, 3-amino-1,2,4-triazole-5-thioethyl, 3-amino-1,2,4-triazole-5-thiopropyl, 4-methyl-5-trifluoromethyl-1,2,4-triazole-3-thioethyl, 4-methyl-5-trifluoromethyl-1,2,4-triazole-3-thiopropyl, 1-methyl-1,2,4-triazole-3-thioethyl, 1-methyl-1,2,4-triazole-3-thiopropyl, 1-methyl-1,2,4-triazole-3-thiobutyl, tetrazole-5-thioethyl, tetrazole-5-thiopropyl, tetrazole-5-thiobutyl, 1-methyl-tetrazole-5-thioethyl, 1-methyl-tetrazole-5-thiopropyl, 1-methyl-tetrazole-5-thiobutyl, 1-(2-dimethylaminoethyl)-tetrazole-5-thioethyl, 1-(2-dimethylaminoethyl)-tetrazole-5-thiopropyl, 1-(2-hydroxyethyl)-tetrazole-5-thioethyl, 1-(2-hydroxyethyl)-tetrazole-5-thiopropyl, 1,3,4-thiadiazole-2-thioethyl, 1,3,4-thiadiazole-2-thiopropyl, 5-methyl-1,3,4-thiadiazole-2-thioethyl, 5-methyl-1,3,4-thiadiazole-2-thiopropyl, 5-methyl-1,3,4-thiadiazole-2-thiobutyl, 5-trifluoromethyl-1,3,4-thiadiazole-2-thioethyl, 5-trifluoromethyl-1,3,4-thiadiazole-2-thiopropyl, 1,2,3-thiadiazole-4-thioethyl, 1,2,3-thiadiazole-4-thiopropyl, 1-carboxymethyl-tetrazole-5-thioethyl, 1-carboxymethyl-tetrazole-5-thiopropyl, 2-pyridyl-thioethyl, 2-pyridyl-thiopropyl, 2-pyridyl-thiobutyl, 4-pyridyl-thioethyl, 4-pyridyl-thiopropyl, 4-pyridyl-thiobutyl, 2-pyrimidine-thioethyl, 2-pyrimidine-thiopropyl, 2-pyrimidine-thiobutyl, 4-amino-pyrimidine-2-thioethyl, 4-amino-pyrimidine-2-thiopropyl, 2-benzimidazole-thioethyl, 2-benzimidazole-thiopropyl, 4-methyl-thiazole-5-thioethyl, 4-methyl-thiazole-5-thiopropyl, 4-methyl-thiazole-5-thiobutyl, 1-methoxycarbonylmethyltetrazole-5-thioethyl, 1-methoxycarbonylmethyltetrazole-5-thiopropyl, 1-methoxycarbonylmethyltetrazole-5-thiobutyl, 5-nitroimidazole-1-thioethyl, 5-nitroimidazole-1-thiopropyl, 5-nitroimidazole-1-thiobutyl, 2-methyl-5-nitroimidazole-1-thioethyl, 2-methyl-5-nitroimidazole-1-thiopropyl and 2-methyl-5-nitroimidazole-1-thiobutyl.

Possible salts for compounds of formula I in which n is the number 0 are all acid addition salts. The pharmacologically tolerated salts of the inorganic and organic acids usually used in pharmaceutical formulations may be mentioned in particular. Salts which are not pharmacologically tolerated and which may initially be obtained as process products, for example during preparation of the compounds according to the invention on an industrial scale, are converted into pharmacologically tolerated salts by processes known to the expert. Suitable such salts are water-soluble and water-insoluble acid addition salts with acids such as, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in the preparation of salts in a ratio of amounts which is equimolar or deviates from equimolar—depending on whether the acid is mono- or polybasic and depending on what salt is desired.

For compounds of formula I in which n is the number 1, suitable salts are also salts with bases. Examples of basic salts which may be mentioned are the lithium, sodium, potassium, calcium, aluminum, magnesium, titanium, ammonium, meglumine or guanidinium salts, it again being possible for the bases to be employed in the salt preparation in a ratio of amounts which is equimolar or deviates from equimolar.

Compounds of formula I which are to be singled out are those in which

R1 is hydrogen,

R2 is hydrogen, halogen or methoxy,

R3 is hydrogen,

R4 is hydrogen,

R5 is hydrogen, 1-4C-alkyl or 1-4C-alkoxy,

R6 is a cyclic radical which is substituted by R8 and R9 and is chosen from the group consisting of benzene, isoxazole, thiazole, imidazole, triazole, tetrazole, thiadiazole, pyridine, pyridine N-oxide, pyrimidine and benzimidazole, R7 is hydrogen or 1-4C-alkyl, R8 is hydrogen, 1-4C-alkyl, hydroxyl, nitro, guanidino, carboxyl, 1-4C-alkoxycarbonyl, 1-4C-alkyl which is substituted by R10, or amino, R9 is hydrogen or 1-4C-alkyl, R10 is hydroxyl, carboxyl, 1-4C-alkoxycarbonyl or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino radical, R13 is hydrogen, 1-4C-alkyl or 1-4C-alkoxy, m is a number from 2 to 4, n is the number 0 or 1, p is the number 0 and q is the number 0, and their salts.

Compounds of formula I which are to be singled out in particular are those in which R1 is hydrogen, R2 is hydrogen, fluorine or methoxy,
R3 is hydrogen,
R4 is hydrogen,
R5 is 1-4C-alkyl or 1-4C-alkoxy,
R6 is a cyclic radical which is substituted by R8 and R9 and is chosen from the group consisting of benzene, thiazole, imidazole, triazole, tetrazole, thiadiazole, pyridine, pyrimidine and benzimidazole,
R7 is hydrogen,
R8 is hydrogen, 1-4C-alkyl, hydroxyl, nitro, guanidino, carboxyl, 1-4C-alkoxycarbonyl, or methyl or ethyl which is substituted by R10,
R9 is hydrogen or 1-4C-alkyl,
R10 is hydroxyl, carboxyl or —N(R11)R12, in which
R11 is 1-4C-alkyl and
R12 is 1-4C-alkyl, or in which
R11 and R12, together and including the nitrogen atom to which they are both bonded, are a piperidino radical,
m is a number from 2 to 4,
n is the number 0,
p is the number 0 and
q is the number 0, and their salts.

Preferred compounds of formula I are those in which
R1 is hydrogen,
R2 is hydrogen or fluorine,
R3 is hydrogen,
R4 is hydrogen,
R5 is 1-4C-alkyl or 1-4C-alkoxy,
R6 is a cyclic radical which is substituted by R8 and R9 and is chosen from the group consisting of benzene, thiazole, imidazole, triazole, tetrazole, thiadiazole, pyridine, pyrimidine and benzimidazole,
R7 is hydrogen,
R8 is hydrogen, methyl, nitro, 1-4C-alkoxycarbonyl, or methyl or ethyl which is substituted by R10,
R9 is hydrogen,
R10 is hydroxyl, carboxyl or —N(R11)R12, in which
R11 is methyl and
R12 is methyl, or in which
R11 and R12, together and including the nitrogen atom to which they are both bonded, are a piperidino radical,
m is a number from 2 to 4,
n is the number 0,
p is the number 0 and
q is the number 0, and their salts.

Particularly preferred compounds of formula I are those in which
R1 is hydrogen,
R2 is hydrogen,
R3 is hydrogen,
R4 is hydrogen,
R5 is 1-4C-alkyl or 1-4C-alkoxy,
R6 is a cyclic radical which is substituted by R8 and R9 and is chosen from the group consisting of benzene, thiazole, imidazole, triazole, tetrazole, thiadiazole, pyridine and pyrimidine,
R7 is hydrogen,
R8 is hydrogen, methyl, or methyl or ethyl which is substituted by R10,
R9 is hydrogen,
R10 is carboxyl or —N(R11)R12, in which
R11 is methyl and
R12 is methyl,
m is a number from 2 to 4,
n is the number 0,
p is the number 0 and
q is the number 0, and their salts.

Examples of compounds according to the invention are listed in the following Table 1, the substituent R1 being in the 5- or 6-position and the substituent R2 being in the 6- or 5-position respectively (because of tautomerism in the benzimidazole ring, no differentiation can be made between positions 5 and 6 if R4=H):

TABLE 1

Compounds of formula I (see FIG. 1A) with the following substituent definitions:

| R1 | R2 | R3 | R4 | R5 | R6 | R7 | m | n | p | q |
|----|----|----|----|----|----|----|----|----|----|----|
| H | H | H | H | H | phenyl | H | 2 | 0 | 0 | 0 |
| H | H | H | H | H | 3-dimethylaminomethylphenyl | H | 2 | 0 | 0 | 0 |
| H | H | H | H | H | 3-piperidinomethylphenyl | H | 2 | 0 | 0 | 0 |
| H | H | H | H | H | 2-thiazolyl | H | 2 | 0 | 0 | 0 |
| H | H | H | H | H | 3,4-dimethyl-2-thiazolyl | H | 2 | 0 | 0 | 0 |
| H | H | H | H | H | 2-imidazolyl | H | 2 | 0 | 0 | 0 |
| H | H | H | H | H | 1-methyl-2-imidazolyl | H | 2 | 0 | 0 | 0 |
| H | H | H | H | H | 1,2,3-triazol-4-yl | H | 2 | 0 | 0 | 0 |
| H | H | H | H | H | 1-methyl-1,2,3-triazol-4-yl | H | 2 | 0 | 0 | 0 |
| H | H | H | H | H | 1,2,4-triazol-3-yl | H | 2 | 0 | 0 | 0 |
| H | H | H | H | H | 4-methyl-1,2,4-triazol-3-yl | H | 2 | 0 | 0 | 0 |
| H | H | H | H | H | tetrazol-5-yl | H | 2 | 0 | 0 | 0 |
| H | H | H | H | H | 1-methyltetrazol-5-yl | H | 2 | 0 | 0 | 0 |
| H | H | H | H | H | 1-(2-dimethylaminoethyl)-tetrazol-5-yl | H | 2 | 0 | 0 | 0 |
| H | H | H | H | H | 1-(2-hydroxyethyl)-tetrazol-5-yl | H | 2 | 0 | 0 | 0 |
| H | H | H | H | H | 1,2,3-thiadiazol-4-yl | H | 2 | 0 | 0 | 0 |
| H | H | H | H | H | 1,3,4-thiadiazol-2-yl | H | 2 | 0 | 0 | 0 |
| H | H | H | H | H | 5-methyl-1,3,4-thiadiazol-2-yl | H | 2 | 0 | 0 | 0 |
| H | H | H | H | H | 2-pyridinyl | H | 2 | 0 | 0 | 0 |
| H | H | H | H | H | 4-pyridinyl | H | 2 | 0 | 0 | 0 |
| H | H | H | H | H | 2-pyrimidinyl | H | 2 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|---|---|---|---|---|---|---|---|---|---|---|
| H | H | H | H | H | 2-benzimidazolyl | H | 2 | 0 | 0 | 0 |
| H | H | H | H | H | 2-furanyl | H | 2 | 0 | 0 | 0 |
| H | H | H | H | H | 2-thienyl | H | 2 | 0 | 0 | 0 |
| H | H | H | H | H | 5-chloro-thiophen-2-yl | H | 2 | 0 | 0 | 0 |
| H | H | H | H | H | 5-(2-dimethylaminomethyl)-furan-2-yl | H | 2 | 0 | 0 | 0 |
| H | H | H | H | H | 5-methyl-furan-2-yl | H | 2 | 0 | 0 | 0 |
| H | H | H | H | H | 2-methyl-5-nitro-1-imidazolyl | H | 2 | 0 | 0 | 0 |
| H | H | H | H | H | 5-nitro-1-imidazolyl | H | 2 | 0 | 0 | 0 |
| H | OCH$_3$ | H | H | H | phenyl | H | 2 | 0 | 0 | 0 |
| H | OCH$_3$ | H | H | H | 3-dimethylaminomethylphenyl | H | 2 | 0 | 0 | 0 |
| H | OCH$_3$ | H | H | H | 3-piperidinomethylphenyl | H | 2 | 0 | 0 | 0 |
| H | OCH$_3$ | H | H | H | 2-thiazolyl | H | 2 | 0 | 0 | 0 |
| H | OCH$_3$ | H | H | H | 3,4-dimethyl-2-thiazolyl | H | 2 | 0 | 0 | 0 |
| H | OCH$_3$ | H | H | H | 2-imidazolyl | H | 2 | 0 | 0 | 0 |
| H | OCH$_3$ | H | H | H | 1-methyl-2-imidazolyl | H | 2 | 0 | 0 | 0 |
| H | OCH$_3$ | H | H | H | 1,2,3-triazol-4-yl | H | 2 | 0 | 0 | 0 |
| H | OCH$_3$ | H | H | H | 1-methyl-1,2,3-triazol-4-yl | H | 2 | 0 | 0 | 0 |
| H | OCH$_3$ | H | H | H | 1,2,4-triazol-3-yl | H | 2 | 0 | 0 | 0 |
| H | OCH$_3$ | H | H | H | 4-methyl-1,2,4-triazol-3-yl | H | 2 | 0 | 0 | 0 |
| H | OCH$_3$ | H | H | H | tetrazol-5-yl | H | 2 | 0 | 0 | 0 |
| H | OCH$_3$ | H | H | H | 1-methyltetrazol-5-yl | H | 2 | 0 | 0 | 0 |
| H | OCH$_3$ | H | H | H | 1-(2-dimethylaminoethyl)-tetrazol-5-yl | H | 2 | 0 | 0 | 0 |
| H | OCH$_3$ | H | H | H | 1-(2-hydroxyethyl)-tetrazol-5-yl | H | 2 | 0 | 0 | 0 |
| H | OCH$_3$ | H | H | H | 1,2,3-thiadiazol-4-yl | H | 2 | 0 | 0 | 0 |
| H | OCH$_3$ | H | H | H | 1,3,4-thiadiazol-2-yl | H | 2 | 0 | 0 | 0 |
| H | OCH$_3$ | H | H | H | 5-methyl-1,3,4-thiadiazol-2-yl | H | 2 | 0 | 0 | 0 |
| H | OCH$_3$ | H | H | H | 2-pyridinyl | H | 2 | 0 | 0 | 0 |
| H | OCH$_3$ | H | H | H | 4-pyridinyl | H | 2 | 0 | 0 | 0 |
| H | OCH$_3$ | H | H | H | 2-pyrimidinyl | H | 2 | 0 | 0 | 0 |
| H | OCH$_3$ | H | H | H | 2-benzimidazolyl | H | 2 | 0 | 0 | 0 |
| H | OCH$_3$ | H | H | H | 2-furanyl | H | 2 | 0 | 0 | 0 |
| H | OCH$_3$ | H | H | H | 2-thienyl | H | 2 | 0 | 0 | 0 |
| H | OCH$_3$ | H | H | H | 5-chloro-thiophen-2-yl | H | 2 | 0 | 0 | 0 |
| H | OCH$_3$ | H | H | H | 5-(2-dimethylaminomethyl)-furan-2-yl | H | 2 | 0 | 0 | 0 |
| H | OCH$_3$ | H | H | H | 5-methyl-furan-2-yl | H | 2 | 0 | 0 | 0 |
| H | OCH$_3$ | H | H | H | 2-methyl-5-nitro-1-imidazolyl | H | 2 | 0 | 0 | 0 |
| H | OCH$_3$ | H | H | H | 5-nitro-1-imidazolyl | H | 2 | 0 | 0 | 0 |
| H | H | H | H | CH$_3$ | phenyl | H | 2 | 0 | 0 | 0 |
| H | H | H | H | CH$_3$ | 3-dimethylaminomethylphenyl | H | 2 | 0 | 0 | 0 |
| H | H | H | H | CH$_3$ | 3-piperidinomethylphenyl | H | 2 | 0 | 0 | 0 |
| H | H | H | H | CH$_3$ | 2-thiazolyl | H | 2 | 0 | 0 | 0 |
| H | H | H | H | CH$_3$ | 3,4-dimethyl-2-thiazolyl | H | 2 | 0 | 0 | 0 |
| H | H | H | H | CH$_3$ | 2-imidazolyl | H | 2 | 0 | 0 | 0 |
| H | H | H | H | CH$_3$ | 1-methyl-2-imidazolyl | H | 2 | 0 | 0 | 0 |
| H | H | H | H | CH$_3$ | 1,2,3-triazol-4-yl | H | 2 | 0 | 0 | 0 |
| H | H | H | H | CH$_3$ | 1-methyl-1,2,3-triazol-4-yl | H | 2 | 0 | 0 | 0 |
| H | H | H | H | CH$_3$ | 1,2,4-triazol-3-yl | H | 2 | 0 | 0 | 0 |
| H | H | H | H | CH$_3$ | 4-methyl-1,2,4-triazol-3-yl | H | 2 | 0 | 0 | 0 |
| H | H | H | H | CH$_3$ | tetrazol-5-yl | H | 2 | 0 | 0 | 0 |
| H | H | H | H | CH$_3$ | 1-methyltetrazol-5-yl | H | 2 | 0 | 0 | 0 |
| H | H | H | H | CH$_3$ | 1-(2-dimethylaminoethyl)-tetrazol-5-yl | H | 2 | 0 | 0 | 0 |
| H | H | H | H | CH$_3$ | 1-(2-hydroxyethyl)-tetrazol-5-yl | H | 2 | 0 | 0 | 0 |
| H | H | H | H | CH$_3$ | 1,2,3-thiadiazol-4-yl | H | 2 | 0 | 0 | 0 |
| H | H | H | H | CH$_3$ | 1,3,4-thiadiazol-2-yl | H | 2 | 0 | 0 | 0 |
| H | H | H | H | CH$_3$ | 5-methyl-1,3,4-thiadiazol-2-yl | H | 2 | 0 | 0 | 0 |
| H | H | H | H | CH$_3$ | 2-pyridinyl | H | 2 | 0 | 0 | 0 |
| H | H | H | H | CH$_3$ | 4-pyridinyl | H | 2 | 0 | 0 | 0 |
| H | H | H | H | CH$_3$ | 2-pyrimidinyl | H | 2 | 0 | 0 | 0 |
| H | H | H | H | CH$_3$ | 2-benzimidazolyl | H | 2 | 0 | 0 | 0 |
| H | H | H | H | CH$_3$ | 2-furanyl | H | 2 | 0 | 0 | 0 |
| H | H | H | H | CH$_3$ | 2-thienyl | H | 2 | 0 | 0 | 0 |
| H | H | H | H | CH$_3$ | 5-chloro-thiophen-2-yl | H | 2 | 0 | 0 | 0 |
| H | H | H | H | CH$_3$ | 5-(2-dimethylaminomethyl)-furan-2-yl | H | 2 | 0 | 0 | 0 |
| H | H | H | H | CH$_3$ | 5-methyl-furan-2-yl | H | 2 | 0 | 0 | 0 |
| H | H | H | H | CH$_3$ | 2-methyl-5-nitro-1-imidazolyl | H | 2 | 0 | 0 | 0 |
| H | H | H | H | CH$_3$ | 5-nitro-1-imidazolyl | H | 2 | 0 | 0 | 0 |
| H | F | H | H | CH$_3$ | phenyl | H | 2 | 0 | 0 | 0 |
| H | F | H | H | CH$_3$ | 3-dimethylaminomethylphenyl | H | 2 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|---|---|---|---|---|---|---|---|---|---|---|
| H | F | H | H | CH₃ | 3-piperidinomethylphenyl | H | 2 | 0 | 0 | 0 |
| H | F | H | H | CH₃ | 2-thiazolyl | H | 2 | 0 | 0 | 0 |
| H | F | H | H | CH₃ | 3,4-dimethyl-2-thiazolyl | H | 2 | 0 | 0 | 0 |
| H | F | H | H | CH₃ | 2-imidazolyl | H | 2 | 0 | 0 | 0 |
| H | F | H | H | CH₃ | 1-methyl-2-imidazolyl | H | 2 | 0 | 0 | 0 |
| H | F | H | H | CH₃ | 1,2,3-triazol-4-yl | H | 2 | 0 | 0 | 0 |
| H | F | H | H | CH₃ | 1-methyl-1,2,3-triazol-4-yl | H | 2 | 0 | 0 | 0 |
| H | F | H | H | CH₃ | 1,2,4-triazol-3-yl | H | 2 | 0 | 0 | 0 |
| H | F | H | H | CH₃ | 4-methyl-1,2,4-triazol-3-yl | H | 2 | 0 | 0 | 0 |
| H | F | H | H | CH₃ | tetrazol-5-yl | H | 2 | 0 | 0 | 0 |
| H | F | H | H | CH₃ | 1-methyltetrazol-5-yl | H | 2 | 0 | 0 | 0 |
| H | F | H | H | CH₃ | 1-(2-dimethylaminoethyl)-tetrazol-5-yl | H | 2 | 0 | 0 | 0 |
| H | F | H | H | CH₃ | 1-(2-hydroxyethyl)-tetrazol-5-yl | H | 2 | 0 | 0 | 0 |
| H | F | H | H | CH₃ | 1,2,3-thiadiazol-4-yl | H | 2 | 0 | 0 | 0 |
| H | F | H | H | CH₃ | 1,3,4-thiadiazol-2-yl | H | 2 | 0 | 0 | 0 |
| H | F | H | H | CH₃ | 5-methyl-1,3,4-thiadiazol-2-yl | H | 2 | 0 | 0 | 0 |
| H | F | H | H | CH₃ | 2-pyridinyl | H | 2 | 0 | 0 | 0 |
| H | F | H | H | CH₃ | 4-pyridinyl | H | 2 | 0 | 0 | 0 |
| H | F | H | H | CH₃ | 2-pyrimidinyl | H | 2 | 0 | 0 | 0 |
| H | F | H | H | CH₃ | 2-benzimidazolyl | H | 2 | 0 | 0 | 0 |
| H | F | H | H | H | 2-furanyl | H | 2 | 0 | 0 | 0 |
| H | F | H | H | H | 2-thienyl | H | 2 | 0 | 0 | 0 |
| H | F | H | H | H | 5-chloro-thiophen-2-yl | H | 2 | 0 | 0 | 0 |
| H | F | H | H | H | 5-(2-dimethylaminomethyl)-furan-2-yl | H | 2 | 0 | 0 | 0 |
| H | F | H | H | H | 5-methyl-furan-2-yl | H | 2 | 0 | 0 | 0 |
| H | F | H | H | H | 2-methyl-5-nitro-1-imidazolyl | H | 2 | 0 | 0 | 0 |
| H | F | H | H | H | 5-nitro-1-imidazolyl | H | 2 | 0 | 0 | 0 |
| H | H | H | H | OCH₃ | phenyl | H | 2 | 0 | 0 | 0 |
| H | H | H | H | OCH₃ | 3-dimethylaminomethylphenyl | H | 2 | 0 | 0 | 0 |
| H | H | H | H | OCH₃ | 3-piperidinomethylphenyl | H | 2 | 0 | 0 | 0 |
| H | H | H | H | OCH₃ | 2-thiazolyl | H | 2 | 0 | 0 | 0 |
| H | H | H | H | OCH₃ | 3,4-dimethyl-2-thiazolyl | H | 2 | 0 | 0 | 0 |
| H | H | H | H | OCH₃ | 2-imidazolyl | H | 2 | 0 | 0 | 0 |
| H | H | H | H | OCH₃ | 1-methyl-2-imidazolyl | H | 2 | 0 | 0 | 0 |
| H | H | H | H | OCH₃ | 1,2,3-triazol-4-yl | H | 2 | 0 | 0 | 0 |
| H | H | H | H | OCH₃ | 1-methyl-1,2,3-triazol-4-yl | H | 2 | 0 | 0 | 0 |
| H | H | H | H | OCH₃ | 1,2,4-triazol-3-yl | H | 2 | 0 | 0 | 0 |
| H | H | H | H | OCH₃ | 4-methyl-1,2,4-triazol-3-yl | H | 2 | 0 | 0 | 0 |
| H | H | H | H | OCH₃ | tetrazol-5-yl | H | 2 | 0 | 0 | 0 |
| H | H | H | H | OCH₃ | 1-methyltetrazol-5-yl | H | 2 | 0 | 0 | 0 |
| H | H | H | H | OCH₃ | 1-(2-dimethylaminoethyl)-tetrazol-5-yl | H | 2 | 0 | 0 | 0 |
| H | H | H | H | OCH₃ | 1-(2-hydroxyethyl)-tetrazol-5-yl | H | 2 | 0 | 0 | 0 |
| H | H | H | H | OCH₃ | 1,2,3-thiadiazol-4-yl | H | 2 | 0 | 0 | 0 |
| H | H | H | H | OCH₃ | 1,3,4-thiadiazol-2-yl | H | 2 | 0 | 0 | 0 |
| H | H | H | H | OCH₃ | 5-methyl-1,3,4-thiadiazol-2-yl | H | 2 | 0 | 0 | 0 |
| H | H | H | H | OCH₃ | 2-pyridinyl | H | 2 | 0 | 0 | 0 |
| H | H | H | H | OCH₃ | 4-pyridinyl | H | 2 | 0 | 0 | 0 |
| H | H | H | H | OCH₃ | 2-pyrimidinyl | H | 2 | 0 | 0 | 0 |
| H | H | H | H | OCH₃ | 2-benzimidazolyl | H | 2 | 0 | 0 | 0 |
| H | H | H | H | OCH₃ | 2-furanyl | H | 2 | 0 | 0 | 0 |
| H | H | H | H | OCH₃ | 2-thienyl | H | 2 | 0 | 0 | 0 |
| H | H | H | H | OCH₃ | 5-chloro-thiophen-2-yl | H | 2 | 0 | 0 | 0 |
| H | H | H | H | OCH₃ | 5-(2-dimethylaminomethyl)-furan-2-yl | H | 2 | 0 | 0 | 0 |
| H | H | H | H | OCH₃ | 5-methyl-furan-2-yl | H | 2 | 0 | 0 | 0 |
| H | H | H | H | OCH₃ | 2-methyl-5-nitro-1-imidazolyl | H | 2 | 0 | 0 | 0 |
| H | H | H | H | OCH₃ | 5-nitro-1-imidazolyl | H | 2 | 0 | 0 | 0 |
| H | H | H | H | H | phenyl | H | 3 | 0 | 0 | 0 |
| H | H | H | H | H | 3-dimethylaminomethylphenyl | H | 3 | 0 | 0 | 0 |
| H | H | H | H | H | 3-piperidinomethylphenyl | H | 3 | 0 | 0 | 0 |
| H | H | H | H | H | 2-thiazolyl | H | 3 | 0 | 0 | 0 |
| H | H | H | H | H | 3,4-dimethyl-2-thiazolyl | H | 3 | 0 | 0 | 0 |
| H | H | H | H | H | 2-imidazolyl | H | 3 | 0 | 0 | 0 |
| H | H | H | H | H | 1-methyl-2-imidazolyl | H | 3 | 0 | 0 | 0 |
| H | H | H | H | H | 1,2,3-triazol-4-yl | H | 3 | 0 | 0 | 0 |
| H | H | H | H | H | 1-methyl-1,2,3-triazol-4-yl | H | 3 | 0 | 0 | 0 |
| H | H | H | H | H | 1,2,4-triazol-3-yl | H | 3 | 0 | 0 | 0 |
| H | H | H | H | H | 4-methyl-1,2,4-triazol-3-yl | H | 3 | 0 | 0 | 0 |
| H | H | H | H | H | tetrazol-5-yl | H | 3 | 0 | 0 | 0 |
| H | H | H | H | H | 1-methyltetrazol-5-yl | H | 3 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|----|----|----|----|----|----|----|---|---|---|---|
| H | H | H | H | H | 1-(2-dimethylaminoethyl)-tetrazol-5-yl | H | 3 | 0 | 0 | 0 |
| H | H | H | H | H | 1-(2-hydroxyethyl)-tetrazol-5-yl | H | 3 | 0 | 0 | 0 |
| H | H | H | H | H | 1,2,3-thiadiazol-4-yl | H | 3 | 0 | 0 | 0 |
| H | H | H | H | H | 1,3,4-thiadiazol-2-yl | H | 3 | 0 | 0 | 0 |
| H | H | H | H | H | 5-methyl-1,3,4-thiadiazol-2-yl | H | 3 | 0 | 0 | 0 |
| H | H | H | H | H | 2-pyridinyl | H | 3 | 0 | 0 | 0 |
| H | H | H | H | H | 4-pyridinyl | H | 3 | 0 | 0 | 0 |
| H | H | H | H | H | 2-pyrimidinyl | H | 3 | 0 | 0 | 0 |
| H | H | H | H | H | 2-benzimidazolyl | H | 3 | 0 | 0 | 0 |
| H | H | H | H | H | 2-furanyl | H | 3 | 0 | 0 | 0 |
| H | H | H | H | H | 2-thienyl | H | 3 | 0 | 0 | 0 |
| H | H | H | H | H | 5-chloro-thiophen-2-yl | H | 3 | 0 | 0 | 0 |
| H | H | H | H | H | 5-(2-dimethylaminomethyl)-furan-2-yl | H | 3 | 0 | 0 | 0 |
| H | H | H | H | H | 5-methyl-furan-2-yl | H | 3 | 0 | 0 | 0 |
| H | H | H | H | H | 2-methyl-5-nitro-1-imidazolyl | H | 3 | 0 | 0 | 0 |
| H | H | H | H | H | 5-nitro-1-imidazolyl | H | 3 | 0 | 0 | 0 |
| H | OCH$_3$ | H | H | H | phenyl | H | 3 | 0 | 0 | 0 |
| H | OCH$_3$ | H | H | H | 3-dimethylaminomethylphenyl | H | 3 | 0 | 0 | 0 |
| H | OCH$_3$ | H | H | H | 3-piperidinomethylphenyl | H | 3 | 0 | 0 | 0 |
| H | OCH$_3$ | H | H | H | 2-thiazolyl | H | 3 | 0 | 0 | 0 |
| H | OCH$_3$ | H | H | H | 3,4-dimethyl-2-thiazolyl | H | 3 | 0 | 0 | 0 |
| H | OCH$_3$ | H | H | H | 2-imidazolyl | H | 3 | 0 | 0 | 0 |
| H | OCH$_3$ | H | H | H | 1-methyl-2-imidazolyl | H | 3 | 0 | 0 | 0 |
| H | OCH$_3$ | H | H | H | 1,2,3-triazol-4-yl | H | 3 | 0 | 0 | 0 |
| H | OCH$_3$ | H | H | H | 1-methyl-1,2,3-triazol-4-yl | H | 3 | 0 | 0 | 0 |
| H | OCH$_3$ | H | H | H | 1,2,4-triazol-3-yl | H | 3 | 0 | 0 | 0 |
| H | OCH$_3$ | H | H | H | 4-methyl-1,2,4-triazol-3-yl | H | 3 | 0 | 0 | 0 |
| H | OCH$_3$ | H | H | H | tetrazol-5-yl | H | 3 | 0 | 0 | 0 |
| H | OCH$_3$ | H | H | H | 1-methyltetrazol-5-yl | H | 3 | 0 | 0 | 0 |
| H | OCH$_3$ | H | H | H | 1-(2-dimethylaminoethyl)-tetrazol-5-yl | H | 3 | 0 | 0 | 0 |
| H | OCH$_3$ | H | H | H | 1-(2-hydroxyethyl)-tetrazol-5-yl | H | 3 | 0 | 0 | 0 |
| H | OCH$_3$ | H | H | H | 1,2,3-thiadiazol-4-yl | H | 3 | 0 | 0 | 0 |
| H | OCH$_3$ | H | H | H | 1,3,4-thiadiazol-2-yl | H | 3 | 0 | 0 | 0 |
| H | OCH$_3$ | H | H | H | 5-methyl-1,3,4-thiadiazol-2-yl | H | 3 | 0 | 0 | 0 |
| H | OCH$_3$ | H | H | H | 2-pyridinyl | H | 3 | 0 | 0 | 0 |
| H | OCH$_3$ | H | H | H | 4-pyridinyl | H | 3 | 0 | 0 | 0 |
| H | OCH$_3$ | H | H | H | 2-pyrimidinyl | H | 3 | 0 | 0 | 0 |
| H | OCH$_3$ | H | H | H | 2-benzimidazolyl | H | 3 | 0 | 0 | 0 |
| H | OCH$_3$ | H | H | H | 2-furanyl | H | 3 | 0 | 0 | 0 |
| H | OCH$_3$ | H | H | H | 2-thienyl | H | 3 | 0 | 0 | 0 |
| H | OCH$_3$ | H | H | H | 5-chloro-thiophen-2-yl | H | 3 | 0 | 0 | 0 |
| H | OCH$_3$ | H | H | H | 5-(2-dimethylaminomethyl)-furan-2-yl | H | 3 | 0 | 0 | 0 |
| H | OCH$_3$ | H | H | H | 5-methyl-furan-2-yl- | H | 3 | 0 | 0 | 0 |
| H | OCH$_3$ | H | H | H | 2-methyl-5-nitro-1-imidazolyl | H | 3 | 0 | 0 | 0 |
| H | OCH$_3$ | H | H | H | 5-nitro-1-imidazolyl | H | 3 | 0 | 0 | 0 |
| H | H | H | H | CH$_3$ | phenyl | H | 3 | 0 | 0 | 0 |
| H | H | H | H | CH$_3$ | 3-dimethylaminomethylphenyl | H | 3 | 0 | 0 | 0 |
| H | H | H | H | CH$_3$ | 3-piperidinomethylphenyl | H | 3 | 0 | 0 | 0 |
| H | H | R | H | CH$_3$ | 2-thiazolyl | H | 3 | 0 | 0 | 0 |
| H | H | H | H | CH$_3$ | 3,4-dimethyl-2-thiazolyl | H | 3 | 0 | 0 | 0 |
| H | H | H | H | CH$_3$ | 2-imidazolyl | H | 3 | 0 | 0 | 0 |
| H | H | H | H | CH$_3$ | 1-methyl-2-imidazolyl | H | 3 | 0 | 0 | 0 |
| H | H | H | H | CH$_3$ | 1,2,3-triazol-4-yl | H | 3 | 0 | 0 | 0 |
| H | H | H | H | CH$_3$ | 1-methyl-1,2,3-triazol-4-yl | H | 3 | 0 | 0 | 0 |
| H | H | H | H | CH$_3$ | 1,2,4-triazol-3-yl | H | 3 | 0 | 0 | 0 |
| H | H | H | H | CH$_3$ | 4-methyl-1,2,4-triazol-3-yl | H | 3 | 0 | 0 | 0 |
| H | H | H | H | CH$_3$ | tetrazol-5-yl | H | 3 | 0 | 0 | 0 |
| H | H | H | H | CH$_3$ | 1-methyltetrazol-5-yl | H | 3 | 0 | 0 | 0 |
| H | H | H | H | CH$_3$ | 1-(2-dimethylaminoethyl)-tetrazol-5-yl | H | 3 | 0 | 0 | 0 |
| H | H | H | H | CH$_3$ | 1-(2-hydroxyethyl)-tetrazol-5-yl | H | 3 | 0 | 0 | 0 |
| H | H | H | H | CH$_3$ | 1,2,3-thiadiazol-4-yl | H | 3 | 0 | 0 | 0 |
| H | H | H | H | CH$_3$ | 1,3,4-thiadiazol-2-yl | H | 3 | 0 | 0 | 0 |
| H | H | H | H | CH$_3$ | 5-methyl-1,3,4-thiadiazol-2-yl | H | 3 | 0 | 0 | 0 |
| H | H | H | H | CH$_3$ | 2-pyridinyl | H | 3 | 0 | 0 | 0 |
| H | H | H | H | CH$_3$ | 4-pyridinyl | H | 3 | 0 | 0 | 0 |
| H | H | H | H | CH$_3$ | 2-pyrimidinyl | H | 3 | 0 | 0 | 0 |
| H | H | H | H | CH$_3$ | 2-benzimidazolyl | H | 3 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|---|---|---|---|---|---|---|---|---|---|---|
| H | H | H | H | CH₃ | 2-furanyl | H | 3 | 0 | 0 | 0 |
| H | H | H | H | CH₃ | 2-thienyl | H | 3 | 0 | 0 | 0 |
| H | H | H | H | CH₃ | 5-chloro-thiophen-2-yl | H | 3 | 0 | 0 | 0 |
| H | H | H | H | CH₃ | 5-(2-dimethylaminomethyl)-furan-2-yl | H | 3 | 0 | 0 | 0 |
| H | H | H | H | CH₃ | 5-methyl-furan-2-yl | H | 3 | 0 | 0 | 0 |
| H | H | H | H | CH₃ | 2-methyl-5-nitro-1-imidazolyl | H | 3 | 0 | 0 | 0 |
| H | H | H | H | CH₃ | 5-nitro-1-imidazolyl | H | 3 | 0 | 0 | 0 |
| H | F | H | H | CH₃ | phenyl | H | 3 | 0 | 0 | 0 |
| H | F | H | H | CH₃ | 3-dimethylaminomethylphenyl | H | 3 | 0 | 0 | 0 |
| H | F | H | H | CH₃ | 3-piperidinomethylphenyl | H | 3 | 0 | 0 | 0 |
| H | F | H | H | CH₃ | 2-thiazolyl | H | 3 | 0 | 0 | 0 |
| H | F | H | H | CH₃ | 3,4-dimethyl-2-thiazolyl | H | 3 | 0 | 0 | 0 |
| H | F | H | H | CH₃ | 2-imidazolyl | H | 3 | 0 | 0 | 0 |
| H | F | H | H | CH₃ | 1-methyl-2-imidazolyl | H | 3 | 0 | 0 | 0 |
| H | F | H | H | CH₃ | 1,2,3-triazol-4-yl | H | 3 | 0 | 0 | 0 |
| H | F | H | H | CH₃ | 1-methyl-1,2,3-triazol-4-yl | H | 3 | 0 | 0 | 0 |
| H | F | H | H | CH₃ | 1,2,4-triazol-3-yl | H | 3 | 0 | 0 | 0 |
| H | F | H | H | CH₃ | 4-methyl-1,2,4-triazol-3-yl | H | 3 | 0 | 0 | 0 |
| H | F | H | H | CH₃ | tetrazol-5-yl | H | 3 | 0 | 0 | 0 |
| H | F | H | H | CH₃ | 1-methyltetrazol-5-yl | H | 3 | 0 | 0 | 0 |
| H | F | H | H | CH₃ | 1-(2-dimethylaminoethyl)-tetrazol-5-yl | H | 3 | 0 | 0 | 0 |
| H | F | H | H | CH₃ | 1-(2-hydroxyethyl)-tetrazol-5-yl | H | 3 | 0 | 0 | 0 |
| H | F | H | H | CH₃ | 1,2,3-thiadiazol-4-yl | H | 3 | 0 | 0 | 0 |
| H | F | H | H | CH₃ | 1,3,4-thiadiazol-2-yl | H | 3 | 0 | 0 | 0 |
| H | F | H | H | CH₃ | 5-methyl-1,3,4-thiadiazol-2-yl | H | 3 | 0 | 0 | 0 |
| H | F | H | H | CH₃ | 2-pyridinyl | H | 3 | 0 | 0 | 0 |
| H | F | H | H | CH₃ | 4-pyridinyl | H | 3 | 0 | 0 | 0 |
| H | F | H | H | CH₃ | 2-pyrimidinyl | H | 3 | 0 | 0 | 0 |
| H | F | H | H | CH₃ | 2-benzimidazolyl | H | 3 | 0 | 0 | 0 |
| H | F | H | H | H | 2-furanyl | H | 3 | 0 | 0 | 0 |
| H | F | H | H | H | 2-thienyl | H | 3 | 0 | 0 | 0 |
| H | F | H | H | H | 5-chloro-thiophen-2-yl | H | 3 | 0 | 0 | 0 |
| H | F | H | H | H | 5-(2-dimethylaminomethyl) furan-2-yl | H | 3 | 0 | 0 | 0 |
| H | F | H | H | H | 5-methyl-furan-2-yl | H | 3 | 0 | 0 | 0 |
| H | F | H | H | H | 2-methyl-5-nitro-1-imidazolyl | H | 3 | 0 | 0 | 0 |
| H | F | H | H | H | 5-nitro-1-imidazolyl | H | 3 | 0 | 0 | 0 |
| H | H | H | H | OCH₃ | phenyl | H | 3 | 0 | 0 | 0 |
| H | H | H | H | OCH₃ | 3-dimethylaminomethylphenyl | H | 3 | 0 | 0 | 0 |
| H | H | H | H | OCH₃ | 3-piperidinomethylphenyl | H | 3 | 0 | 0 | 0 |
| H | H | H | H | OCH₃ | 2-thiazolyl | H | 3 | 0 | 0 | 0 |
| H | H | H | H | OCH₃ | 3,4-dimethyl-2-thiazolyl | H | 3 | 0 | 0 | 0 |
| H | H | H | H | OCH₃ | 2-imidazolyl | H | 3 | 0 | 0 | 0 |
| H | H | H | H | OCH₃ | 1-methyl-2-imidazolyl | H | 3 | 0 | 0 | 0 |
| H | H | H | H | OCH₃ | 1,2,3-triazol-4-yl | H | 3 | 0 | 0 | 0 |
| H | H | H | H | OCH₃ | 1-methyl-1,2,3-triazol-4-yl | H | 3 | 0 | 0 | 0 |
| H | H | H | H | OCH₃ | 1,2,4-triazol-3-yl | H | 3 | 0 | 0 | 0 |
| H | H | H | H | OCH₃ | 4-methyl-1,2,4-triazol-3-yl | H | 3 | 0 | 0 | 0 |
| H | H | H | H | OCH₃ | tetrazol-5-yl | H | 3 | 0 | 0 | 0 |
| H | H | H | H | OCH₃ | 1-methyltetrazol-5-yl | H | 3 | 0 | 0 | 0 |
| H | H | H | H | OCH₃ | 1-(2-dimethylaminoethyl)-tetrazol-5-yl | H | 3 | 0 | 0 | 0 |
| H | H | H | H | OCH₃ | 1-(2-hydroxyethyl)-tetrazol-5-yl | H | 3 | 0 | 0 | 0 |
| H | H | H | H | OCH₃ | 1,2,3-thiadiazol-4-yl | H | 3 | 0 | 0 | 0 |
| H | H | H | H | OCH₃ | 1,3,4-thiadiazol-2-yl | H | 3 | 0 | 0 | 0 |
| H | H | H | H | OCH₃ | 5-methyl-1,3,4-thiadiazol-2-yl | H | 3 | 0 | 0 | 0 |
| H | H | H | H | OCH₃ | 2-pyridinyl | H | 3 | 0 | 0 | 0 |
| H | H | H | H | OCH₃ | 4-pyridinyl | H | 3 | 0 | 0 | 0 |
| H | H | H | H | OCH₃ | 2-pyrimidinyl | H | 3 | 0 | 0 | 0 |
| H | H | H | H | OCH₃ | 2-benzimidazolyl | H | 3 | 0 | 0 | 0 |
| H | H | H | H | OCH₃ | 2-furanyl | H | 3 | 0 | 0 | 0 |
| H | H | H | H | OCH₃ | 2-thienyl | H | 3 | 0 | 0 | 0 |
| H | H | H | H | OCH₃ | 5-chloro-thiophen-2-yl | H | 3 | 0 | 0 | 0 |
| H | H | H | H | OCH₃ | 5-(2-dimethylaminomethyl)-furan-2-yl | H | 3 | 0 | 0 | 0 |
| H | H | H | H | OCH₃ | 5-methyl-furan-2-yl | H | 3 | 0 | 0 | 0 |
| H | H | H | H | OCH₃ | 2-methyl-5-nitro-1-imidazolyl | H | 3 | 0 | 0 | 0 |
| H | H | H | H | OCH₃ | 5-nitro-1-imidazolyl | H | 3 | 0 | 0 | 0 |
| H | H | H | H | H | phenyl | H | 4 | 0 | 0 | 0 |
| H | H | H | H | H | 3-dimethylaminomethylphenyl | H | 4 | 0 | 0 | 0 |
| H | H | H | H | H | 3-piperidinomethylphenyl | H | 4 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|---|---|---|---|---|---|---|---|---|---|---|
| H | H | H | H | H | 2-thiazolyl | H | 4 | 0 | 0 | 0 |
| H | H | H | H | H | 3,4-dimethyl-2-thiazolyl | H | 4 | 0 | 0 | 0 |
| H | H | H | H | H | 2-imidazolyl | H | 4 | 0 | 0 | 0 |
| H | H | H | H | H | 1-methyl-2-imidazolyl | H | 4 | 0 | 0 | 0 |
| H | H | H | H | H | 1,2,3-triazol-4-yl | H | 4 | 0 | 0 | 0 |
| H | H | H | H | H | 1-methyl-1,2,3-triazol-4-yl | H | 4 | 0 | 0 | 0 |
| H | H | H | H | H | 1,2,4-triazol-3-yl | H | 4 | 0 | 0 | 0 |
| H | H | H | H | H | 4-methyl-1,2,4-triazol-3-yl | H | 4 | 0 | 0 | 0 |
| H | H | H | H | H | tetrazol-5-yl | H | 4 | 0 | 0 | 0 |
| H | H | H | H | H | 1-methyltetrazol-5-yl | H | 4 | 0 | 0 | 0 |
| H | H | H | H | H | 1-(2-dimethylaminoethyl)-tetrazol-5-yl | H | 4 | 0 | 0 | 0 |
| H | H | H | H | H | 1-(2-hydroxyethyl)-tetrazol-5-yl | H | 4 | 0 | 0 | 0 |
| H | H | H | H | H | 1,2,3-thiadiazol-4-yl | H | 4 | 0 | 0 | 0 |
| H | H | H | H | H | 1,3,4-thiadiazol-2-yl | H | 4 | 0 | 0 | 0 |
| H | H | H | H | H | 5-methyl-1,3,4-thiadiazol-2-yl | H | 4 | 0 | 0 | 0 |
| H | H | H | H | H | 2-pyridinyl | H | 4 | 0 | 0 | 0 |
| H | H | H | H | H | 4-pyridinyl | H | 4 | 0 | 0 | 0 |
| H | H | H | H | H | 2-pyrimidinyl | H | 4 | 0 | 0 | 0 |
| H | H | H | H | H | 2-benzimidazolyl | H | 4 | 0 | 0 | 0 |
| H | H | H | H | H | 2-furanyl | H | 4 | 0 | 0 | 0 |
| H | H | H | H | H | 2-thienyl | H | 4 | 0 | 0 | 0 |
| H | H | H | H | H | 5-chloro-thiophen-2-yl | H | 4 | 0 | 0 | 0 |
| H | H | H | H | H | 5-(2-dimethylaminomethyl)-furan-2-yl | H | 4 | 0 | 0 | 0 |
| H | H | H | H | H | 5-methyl-furan-2-yl | H | 4 | 0 | 0 | 0 |
| H | H | H | H | H | 2-methyl-5-nitro-1-imidazolyl | H | 4 | 0 | 0 | 0 |
| H | H | H | H | H | 5-nitro-1-imidazolyl | H | 4 | 0 | 0 | 0 |
| H | OCH$_3$ | H | H | H | phenyl | H | 4 | 0 | 0 | 0 |
| H | OCH$_3$ | H | H | H | 3-dimethylaminomethylphenyl | H | 4 | 0 | 0 | 0 |
| H | OCH$_3$ | H | H | H | 3-piperidinomethylphenyl | H | 4 | 0 | 0 | 0 |
| H | OCH$_3$ | H | H | H | 2-thiazolyl | H | 4 | 0 | 0 | 0 |
| H | OCH$_3$ | H | H | H | 3,4-dimethyl-2-thiazolyl | H | 4 | 0 | 0 | 0 |
| H | OCH$_3$ | H | H | H | 2-imidazolyl | H | 4 | 0 | 0 | 0 |
| H | OCH$_3$ | H | H | H | 1-methyl-2-imidazolyl | H | 4 | 0 | 0 | 0 |
| H | OCH$_3$ | H | H | H | 1,2,3-triazol-4-yl | H | 4 | 0 | 0 | 0 |
| H | OCH$_3$ | H | H | H | 1-methyl-1,2,3-triazol-4-yl | H | 4 | 0 | 0 | 0 |
| H | OCH$_3$ | H | H | H | 1,2,4-triazol-3-yl | H | 4 | 0 | 0 | 0 |
| H | OCH$_3$ | H | H | H | 4-methyl-1,2,4-triazol-3-yl | H | 4 | 0 | 0 | 0 |
| H | OCH$_3$ | H | H | H | tetrazol-5-yl | H | 4 | 0 | 0 | 0 |
| H | OCH$_3$ | H | H | H | 1-methyltetrazol-5-yl | H | 4 | 0 | 0 | 0 |
| H | OCH$_3$ | H | H | H | 1-(2-dimethylaminoethyl)-tetrazol-5-yl | H | 4 | 0 | 0 | 0 |
| H | OCH$_3$ | H | H | H | 1-(2-hydroxyethyl)-tetrazol-5-yl | H | 4 | 0 | 0 | 0 |
| H | OCH$_3$ | H | H | H | 1,2,3-thiadiazol-4-yl | H | 4 | 0 | 0 | 0 |
| H | OCH$_3$ | H | H | H | 1,3,4-thiadiazol-2-yl | H | 4 | 0 | 0 | 0 |
| H | OCH$_3$ | H | H | H | 5-methyl-1,3,4-thiadiazol-2-yl | H | 4 | 0 | 0 | 0 |
| H | OCH$_3$ | H | H | H | 2-pyridinyl | H | 4 | 0 | 0 | 0 |
| H | OCH$_3$ | H | H | H | 4-pyridinyl | H | 4 | 0 | 0 | 0 |
| H | OCH$_3$ | H | H | H | 2-pyrimidinyl | H | 4 | 0 | 0 | 0 |
| H | OCH$_3$ | H | H | H | 2-benzimidazolyl | H | 4 | 0 | 0 | 0 |
| H | OCH$_3$ | H | H | H | 2-furanyl | H | 4 | 0 | 0 | 0 |
| H | OCH$_3$ | H | H | H | 2-thienyl | H | 4 | 0 | 0 | 0 |
| H | OCH$_3$ | H | H | H | 5-chloro-thiophen-2-yl | H | 4 | 0 | 0 | 0 |
| H | OCH$_3$ | H | H | H | 5-(2-dimethylaminomethyl)-furan-2-yl | H | 4 | 0 | 0 | 0 |
| H | OCH$_3$ | H | H | H | 5-methyl-furan-2-yl | H | 4 | 0 | 0 | 0 |
| H | OCH$_3$ | H | H | H | 2-methyl-5-nitro-1-imidazolyl | H | 4 | 0 | 0 | 0 |
| H | OCH$_3$ | H | H | H | 5-nitro-1-imidazolyl | H | 4 | 0 | 0 | 0 |
| H | H | H | H | CH$_3$ | phenyl | H | 4 | 0 | 0 | 0 |
| H | H | H | H | CH$_3$ | 3-dimethylaminomethylphenyl | H | 4 | 0 | 0 | 0 |
| H | H | H | H | CH$_3$ | 3-piperidinomethylphenyl | H | 4 | 0 | 0 | 0 |
| H | H | H | H | CH$_3$ | 2-thiazolyl | H | 4 | 0 | 0 | 0 |
| H | H | H | H | CH$_3$ | 3,4-dimethyl-2-thiazolyl | H | 4 | 0 | 0 | 0 |
| H | H | H | H | CH$_3$ | 2-imidazolyl | H | 4 | 0 | 0 | 0 |
| H | H | H | H | CH$_3$ | 1-methyl-2-imidazolyl | H | 4 | 0 | 0 | 0 |
| H | H | H | H | CH$_3$ | 1,2,3-triazol-4-yl | H | 4 | 0 | 0 | 0 |
| H | H | H | H | CH$_3$ | 1-methyl-1,2,3-triazol-4-yl | H | 4 | 0 | 0 | 0 |
| H | H | H | H | CH$_3$ | 1,2,4-triazol-3-yl | H | 4 | 0 | 0 | 0 |
| H | H | H | H | CH$_3$ | 4-methyl-1,2,4-triazol-3-yl | H | 4 | 0 | 0 | 0 |
| H | H | H | H | CH$_3$ | tetrazol-5-yl | H | 4 | 0 | 0 | 0 |
| H | H | H | H | CH$_3$ | 1-methyltetrazol-5-yl | H | 4 | 0 | 0 | 0 |
| H | H | H | H | CH$_3$ | 1-(2-dimethylaminoethyl)-tetra- | H | 4 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|---|---|---|---|---|---|---|---|---|---|---|
| | | | | | zol-5-yl | | | | | |
| H | H | H | H | CH$_3$ | 1-(2-hydroxyethyl)-tetrazol-5-yl | H | 4 | 0 | 0 | 0 |
| H | H | H | H | CH$_3$ | 1,2,3-thiadiazol-4-yl | H | 4 | 0 | 0 | 0 |
| H | H | H | H | CH$_3$ | 1,3,4-thiadiazol-2-yl | H | 4 | 0 | 0 | 0 |
| H | H | H | H | CH$_3$ | 5-methyl-1,3,4-thiadiazol-2-yl | H | 4 | 0 | 0 | 0 |
| H | H | H | H | CH$_3$ | 2-pyridinyl | H | 4 | 0 | 0 | 0 |
| H | H | H | H | CH$_3$ | 4-pyridinyl | H | 4 | 0 | 0 | 0 |
| H | H | H | H | CH$_3$ | 2-pyrimidinyl | H | 4 | 0 | 0 | 0 |
| H | H | H | H | CH$_3$ | 2-benzimidazolyl | H | 4 | 0 | 0 | 0 |
| H | H | H | H | CH$_3$ | 2-furanyl | H | 4 | 0 | 0 | 0 |
| H | H | H | H | CH$_3$ | 2-thienyl | H | 4 | 0 | 0 | 0 |
| H | H | H | H | CH$_3$ | 5-chloro-thiophen-2-yl | H | 4 | 0 | 0 | 0 |
| H | H | H | H | CH$_3$ | 5-(2-dimethylaminomethyl)-furan-2-yl | H | 4 | 0 | 0 | 0 |
| H | H | H | H | CH$_3$ | 5-methyl-furan-2-yl | H | 4 | 0 | 0 | 0 |
| H | H | H | H | CH$_3$ | 2-methyl-5-nitro-1-imidazolyl | H | 4 | 0 | 0 | 0 |
| H | H | H | H | CH$_3$ | 5-nitro-1-imidazolyl | H | 4 | 0 | 0 | 0 |
| H | F | H | H | CH$_3$ | phenyl | H | 4 | 0 | 0 | 0 |
| H | F | H | H | CH$_3$ | 3-dimethylaminomethylphenyl | H | 4 | 0 | 0 | 0 |
| H | F | H | H | CH$_3$ | 3-piperidinomethylphenyl | H | 4 | 0 | 0 | 0 |
| H | F | H | H | CH$_3$ | 2-thiazolyl | H | 4 | 0 | 0 | 0 |
| H | F | H | H | CH$_3$ | 3,4-dimethyl-2-thiazolyl | H | 4 | 0 | 0 | 0 |
| H | F | H | H | CH$_3$ | 2-imidazolyl | H | 4 | 0 | 0 | 0 |
| H | F | H | H | CH$_3$ | 1-methyl-2-imidazolyl | H | 4 | 0 | 0 | 0 |
| H | F | H | H | CH$_3$ | 1,2,3-triazol-4-yl | H | 4 | 0 | 0 | 0 |
| H | F | H | H | CH$_3$ | 1-methyl-1,2,3-triazol-4-yl | H | 4 | 0 | 0 | 0 |
| H | F | H | H | CH$_3$ | 1,2,4-triazol-3-yl | H | 4 | 0 | 0 | 0 |
| H | F | H | H | CH$_3$ | 4-methyl-1,2,4-triazol-3-yl | H | 4 | 0 | 0 | 0 |
| H | F | H | H | CH$_3$ | tetrazol-5-yl | H | 4 | 0 | 0 | 0 |
| H | F | H | H | CH$_3$ | 1-methyltetrazol-5-yl | H | 4 | 0 | 0 | 0 |
| H | F | H | H | CH$_3$ | 1-(2-dimethylaminoethyl)-tetrazol-5-yl | H | 4 | 0 | 0 | 0 |
| H | F | H | H | CH$_3$ | 1-(2-hydroxyethyl)-tetrazol-5-yl | H | 4 | 0 | 0 | 0 |
| H | F | H | H | CH$_3$ | 1,2,3-thiadiazol-4-yl | H | 4 | 0 | 0 | 0 |
| H | F | H | H | CH$_3$ | 1,3,4-thiadiazol-2-yl | H | 4 | 0 | 0 | 0 |
| H | F | H | H | CH$_3$ | 5-methyl-1,3,4-thiadiazol-2-yl | H | 4 | 0 | 0 | 0 |
| H | F | H | H | CH$_3$ | 2-pyridinyl | H | 4 | 0 | 0 | 0 |
| H | F | H | H | CH$_3$ | 4-pyridinyl | H | 4 | 0 | 0 | 0 |
| H | F | H | H | CH$_3$ | 2-pyrimidinyl | H | 4 | 0 | 0 | 0 |
| H | F | H | H | CH$_3$ | 2-benzimidazolyl | H | 4 | 0 | 0 | 0 |
| H | F | H | H | CH$_3$ | 2-furanyl | H | 4 | 0 | 0 | 0 |
| H | F | H | H | CH$_3$ | 2-thienyl | H | 4 | 0 | 0 | 0 |
| H | F | H | H | CH$_3$ | 5-chloro-thiophen-2-yl | H | 4 | 0 | 0 | 0 |
| H | F | H | H | CH$_3$ | 5-(2-dimethylaminomethyl)-furan-2-yl | H | 4 | 0 | 0 | 0 |
| H | F | H | H | CH$_3$ | 5-methyl-furan-2-yl | H | 4 | 0 | 0 | 0 |
| H | F | H | H | CH$_3$ | 2-methyl-5-nitro-1-imidazolyl | H | 4 | 0 | 0 | 0 |
| H | F | H | H | CH$_3$ | 5-nitro-1-imidazolyl | H | 4 | 0 | 0 | 0 |
| H | H | H | H | OCH$_3$ | phenyl | H | 4 | 0 | 0 | 0 |
| H | H | H | H | OCH$_3$ | 3-dimethylaminomethylphenyl | H | 4 | 0 | 0 | 0 |
| H | H | H | H | OCH$_3$ | 3-piperidinomethylphenyl | H | 4 | 0 | 0 | 0 |
| H | H | H | H | OCH$_3$ | 2-thiazolyl | H | 4 | 0 | 0 | 0 |
| H | H | H | H | OCH$_3$ | 3,4-dimethyl-2-thiazolyl | H | 4 | 0 | 0 | 0 |
| H | H | H | H | OCH$_3$ | 2-imidazolyl | H | 4 | 0 | 0 | 0 |
| H | H | H | H | OCH$_3$ | 1-methyl-2-imidazolyl | H | 4 | 0 | 0 | 0 |
| H | H | H | H | OCH$_3$ | 1,2,3-triazol-4-yl | H | 4 | 0 | 0 | 0 |
| H | H | H | H | OCH$_3$ | 1-methyl-1,2,3-triazol-4-yl | H | 4 | 0 | 0 | 0 |
| H | H | H | H | OCH$_3$ | 1,2,4-triazol-3-yl | H | 4 | 0 | 0 | 0 |
| H | H | H | H | OCH$_3$ | 4-methyl-1,2,4-triazol-3-yl | H | 4 | 0 | 0 | 0 |
| H | H | H | H | OCH$_3$ | tetrazol-5-yl | H | 4 | 0 | 0 | 0 |
| H | H | H | H | OCH$_3$ | 1-methyltetrazol-5-yl | H | 4 | 0 | 0 | 0 |
| H | H | H | H | OCH$_3$ | 1-(2-dimethylaminoethyl)-tetrazol-5-yl | H | 4 | 0 | 0 | 0 |
| H | H | H | H | OCH$_3$ | 1-(2-hydroxyethyl)-tetrazol-5-yl | H | 4 | 0 | 0 | 0 |
| H | H | H | H | OCH$_3$ | 1,2,3-thiadiazol-4-yl | H | 4 | 0 | 0 | 0 |
| H | H | H | H | OCH$_3$ | 1,3,4-thiadiazol-2-yl | H | 4 | 0 | 0 | 0 |
| H | H | H | H | OCH$_3$ | 5-methyl-1,3,4-thiadiazol-2-yl | H | 4 | 0 | 0 | 0 |
| H | H | H | H | OCH$_3$ | 2-pyridinyl | H | 4 | 0 | 0 | 0 |
| H | H | H | H | OCH$_3$ | 4-pyridinyl | H | 4 | 0 | 0 | 0 |
| H | H | H | H | OCH$_3$ | 2-pyrimidinyl | H | 4 | 0 | 0 | 0 |
| H | H | H | H | OCH$_3$ | 2-benzimidazolyl | H | 4 | 0 | 0 | 0 |
| H | H | H | H | OCH$_3$ | 2-furanyl | H | 4 | 0 | 0 | 0 |

TABLE 1-continued

Compounds of formula I (see FIG. 1A) with the following substituent definitions:

| R1 | R2 | R3 | R4 | R5 | R6 | R7 | m | n | p | q |
|----|----|----|----|----|----|----|---|---|---|---|
| H | H | H | H | OCH$_3$ | 2-thienyl | H | 4 | 0 | 0 | 0 |
| H | H | H | H | OCH$_3$ | 5-chloro-thiophen-2-yl | H | 4 | 0 | 0 | 0 |
| H | H | H | H | OCH$_3$ | 5-(2-dimethylaminomethyl)-furan-2-yl | H | 4 | 0 | 0 | 0 |
| H | H | H | H | OCH$_3$ | 5-methyl-furan-2-yl | H | 4 | 0 | 0 | 0 |
| H | H | H | H | OCH$_3$ | 2-methyl-5-nitro-1-imidazolyl | H | 4 | 0 | 0 | 0 |
| H | H | H | H | OCH$_3$ | 5-nitro-1-imidazolyl | H | 4 | 0 | 0 | 0 | and the salts of these compounds in the tables.

The invention furthermore relates to a process for the preparation of the compounds of formula I in which R1, R2, R3, R4, R5, R6, R7, m, n, p and q have the abovementioned meanings, and their salts.

Figure 1B:
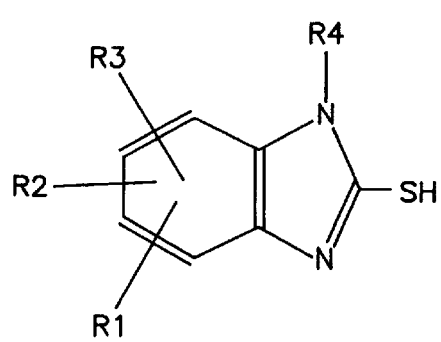
FIG. 1B, FIG. 1C and FIG. 1D are formulae of intermediates for preparing that final product.
Figure 1C:
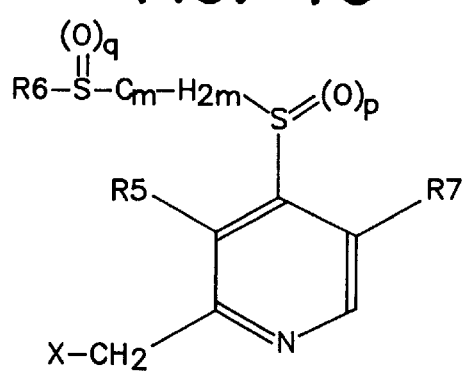
Figure 1D:
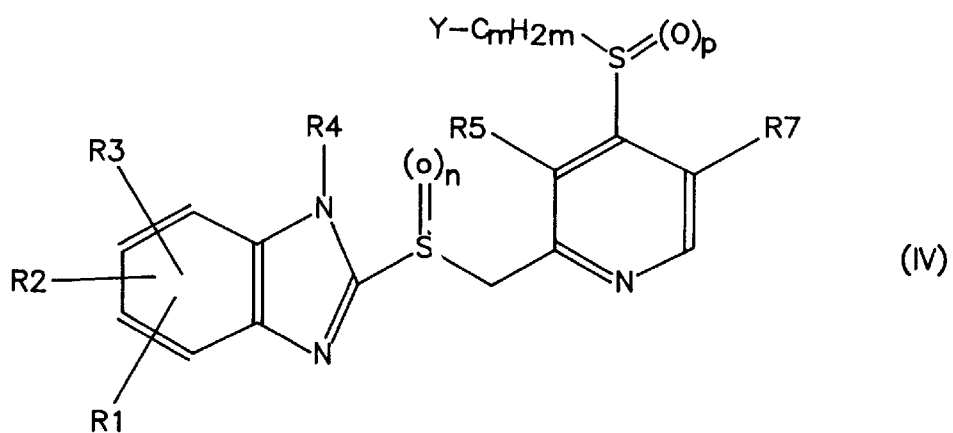

The process comprises
a) reacting mercaptobenzimidazoles of formula II (see FIG. 1B), in which R1, R2, R3 and R4 have the abovementioned meanings, with picoline derivatives III (see FIG. 1C), in which R5, R6, R7, m, p and q have the abovementioned meanings and X is a suitable leaving group, or
b) reacting compounds of formula IV (see FIG. 1D), in which R1, R2, R3, R4, R5, R7 and m have the abovementioned meanings, n and p are the number 0 and Y is a suitable leaving group, with thiols R6-SH, and (if compounds of formula I where n=1 or p=1 and/or q=1 are the desired end products), subsequently oxidizing the compounds obtained according to a) or b) where n=0 and/or p=0 and/or q=0, and/or if desired subsequently converting compounds obtained into the salts, and/or if desired subsequently converting salts obtained into the free compounds.

The starting compounds can be employed as such or, where appropriate, in the form of their salts in the abovementioned reaction.

Examples which may be mentioned of suitable leaving groups X and Y are halogen atoms, in particular chlorine, or hydroxyl groups activated by esterification (for example with p-toluenesulfonic acid).

The reaction of II with III is carried out in suitable, preferably polar protic or aprotic solvents (such as methanol, ethanol, isopropanol, dimethyl sulfoxide, acetone, dimethylformamide or acetonitrile), with the addition of or exclusion of water. It is carried out, for example, in the presence of a proton acceptor. Suitable proton acceptors are alkali metal hydroxides, such as sodium hydroxide, alkali metal carbonates, such as potassium carbonate, or tertiary amines, such as pyridine, triethylamine or ethyldiisopropylamine. Alternatively, the reaction can also be carried out without a proton acceptor, in which case, where appropriate—depending on the nature of the starting compounds—the acid addition salts can initially be separated off in a particularly pure form. The reaction temperature can be between 0° and 150° C., temperatures between 20° and 80° C. being preferred in the presence of proton acceptors and temperatures between 60° and 120° C.—in particular the boiling point of the solvents used—being preferred without proton acceptors. The reaction times are between 0.5 and 30 hours.

The reaction of compounds IV with thiols R6-SH is carried out in a similar manner to the reaction of compounds II with compounds III.

The oxidation of the sulfides (compounds of formula I where n=0) to give the sulfoxides (compounds of formula I where n=1) is carried out under the conditions which are familiar to the expert for the oxidation of sulfides to sulfoxides [in this context, cf., for example, J. Drabowicz and M. Mikolajczyk, Organic Preparations and Procedures Int. 14(1–2), 45–89 (1982) or E. Block in S. Patai, The Chemistry of Functional Groups, Supplement E. Part 1, pages 539–608, John Wiley and Sons (Interscience Publication), 1980]. Possible oxidizing agents are all the reagents usually used for the oxidation of sulfides to sulfoxides, in particular peroxy acids, such as, peroxyacetic acid, trifluoroperoxyacetic acid, 3,5-dinitroperoxybenzoic acid, peroxymaleic acid, magnesium monoperoxyphthalate or, preferably, m-chloroperoxybenzoic acid.

The reaction temperature is between −70° C. and the boiling point of the solvent used (depending on the reactivity of the oxidizing agent and the degree of dilution), but preferably between −30° and +20° C. Oxidation with halogens or with hypohalites (for example with aqueous sodium hypochlorite solution), which is expediently carried out at temperatures between 0° and 50° C., has also proved advantageous. The reaction is expediently carried out in inert solvents, for example aromatic or chlorinated hydrocarbons, such as benzene, toluene, methylene chloride or chloroform, but preferably in esters or ethers, such as ethyl acetate, isopropyl acetate or dioxane, or in alcohols, preferably isopropanol.

The sulfoxides according to the invention are optically active compounds. Further chirality centers may also be present in the molecule, depending on the nature of the substituents. The invention therefore relates both to the enantiomers and diastereomers and to their mixtures and racemates. The enantiomers can be separated in a manner known per se (for example by the preparation and separation of corresponding diastereomeric compounds; cf. for example, WO92/08716).

Compounds II are known, for example, from WO86/02646, EP 134 400 or EP 127 763. Compounds III where p=0 and/or q=0 can be prepared, for example, as described in the following examples.

For compounds III where p=1 and/or q=1, the corresponding 2-hydroxymethyl-4-mercapto-substituted pyridines are oxidized, for example, with m-chloroperoxybenzoic acid to give the sulfoxides, and these are then chlorinated, for example with thionyl chloride. Reaction with 2-mercaptobenzimidazoles gives compounds of formula I where p=1 and q=1.

Depending on the nature of the substituent R6, the sulfoxides where q=1 are also obtained during oxidation to the sulfoxides where n=1. Otherwise, the respective sulfides or sulfoxides can be prepared by choosing suitable starting compounds or by using selective oxidizing agents.

The thiols R6-C$_m$H$_{2m}$-SH required for the preparation of III can be prepared, for example, from the corresponding halogen compounds analogously to J. Med. Chem. 14 (1971) 349.

The following examples illustrate the invention in more detail without limiting it. The compounds according to the invention and the starting compounds can be prepared in a manner analogous to that described in the examples.

EXAMPLES

End Products 1. 2-{[[3-Methyl-4-(3-(5-methyl-1,3,4-thiadiazol-2-yl-thio}-propylthio)-2-pyridinyl]methyl]thiol-1H-benzimidazole 2-{[[4-(3-Chloropropylthio)-3-methyl-2-pyridinyl]-methyl]thio}-1H-benzimidazole (0.36 g, 1.0 mmol) is added to a solution of 5-methyl-1,3,4-thiadiazole-2-thiol (0.16 g, 1.2 mmol) in 10 ml of ethanol and 1.4 ml of 1N sodium hydroxide solution and the mixture is heated at the boiling point under reflux for 20–30 hours. 12 ml of H$_2$O are added dropwise, the mixture is allowed to cool, and the solid which has precipitated out is filtered off, washed with water and dried in vacuo at 50° C. 0.38 g (83% of theory) of the title compound is obtained as a colorless solid of melting point 76°–77° C.

2. 2-{[[3-Methyl-4-(3-(4-methyl-1,2,4-triazol-3-yl-thio)-propylthio)-2-pyridinyl]methyl]thio}-1H-benzimidazole By the procedure described in Example 1, the crude title compound (containing water) is obtained by reaction of 4-methyl-1,2,4-triazole-3-thiol (0.19 g, 1.6 mmol) and 2-{[[4-(3-chloropropylthio)-3-methyl-2-pyridinyl]methyl]thio}-1H-benzimidazole (0.36 g, 1.0 mmol) and 1.7 mmol of 1N sodium hydroxide solution. After crystallization from ethyl acetate/diisopropyl ether, the title compound is obtained as a colorless solid of melting point 98°–99° C. (yield 58% of theory).

3. 2-{[[3-Methyl-4-(3-(1-methylimidazol-2-yl-thio)-propylthio)-2-pyridinyl]methyl]thio}-1H-benzimidazole By the procedure described in Example 1, the title compound (68% of theory) is obtained as a colorless solid of melting point 97°–99° C. by reaction of 2-mercapto-1-methylimidazole with 2-{[[4-(3-chloropropylthio)-3-methyl-2-pyridinyl]methyl]thio}-1H-benzimidazole and NaOH followed by crystallization from ethyl acetate/diisopropyl ether.

4. 2-{[[4-[3-(3-Amino-1,2,4-triazol-5-yl-thio)-propylthio]-3-methyl-2-pyridinyl]methyl]thio}-1H-benzimidazole By the procedure described in Example 1, the title compound (82% of theory) is obtained as a colorless solid of melting point 94°–96° C. by reaction of 3-amino-5-mercapto-1,2,4-triazole with 2-{[[4-(3-chloropropylthio)-3-methyl-2-pyridinyl]methyl]thio}-1H-benzimidazole and NaOH.

5. 2-{[[4-[3-(5-Amino-1,3,4-thiadiazol-2-yl-thio)-propylthio]-3-methyl-2-pyridinyl]methyl]thio}-1H-benzimidazole By the procedure described in Example 1, the crude title compound is obtained as a oil by reaction of 2-amino-5-mercapto-1,3,4-thiadiazole with 2-{[[4-(3-chloropropylthio)-3-methyl-2-pyridinyl]methyl]thio}-1H-benzimidazole and NaOH. The title compound is obtained as the trihydrochloride by dissolving in isopropanol, adding concentrated hydrochloric acid (about 5 equivalents), evaporating to dryness and triturating the residue with acetone; colorless solid; 105° C., evolution of gas; above 240° C., decomposition.

6. 2-{[[4-[3-Imidazol-2-yl-thio-propylthio]-3-methyl-2-pyridinyl]methyl]thio}-1H-benzimidazole By the procedure described in Example 1, the title compound (62% of theory) is obtained by reaction of 2-mercaptoimidazole with 2-{[[4-(3-chloropropylthio)-3-methyl-2-pyridinyl]methyl]thio}-1H-benzimidazole and NaOH followed by recrystallization from methanol/toluene; colorless solid of melting point 195° C. (decomposition).

7. 2-{[[3-Methyl-4-(3-(1,2,4-triazol-3-yl-thio)-propylthio)-2-pyridinyl]methyl]thio}-1H-benzimidazole By the procedure described in Example 1, the title compound (76% of theory) is obtained by reaction of 3-mercapto-1,2,4-triazole with 2-{[[4-(3-chloropropylthio)-3-methyl-2-pyridinyl]methyl]thio}-1H-benzimidazole and NaOH; colorless solid of melting point 80°–82° C.

8. 2-{[[3-Methyl-4-(3-(1-methyl-tetrazol-5-yl-thio)-propylthio)-2-pyridinyl]methyl]thio}-1H-benzimidazole By the procedure described in Example 1, the title compound (68% of theory) is obtained by reaction of 1-methyl-5-mercaptotetrazole with 2-{[[4-(3-chloropropylthio)-3-methyl-2-pyridinyl]methyl]thio}-1H-benzimidazole and NaOH; colorless solid of melting point 99°–103° C.

9. 2-{[[3-Methyl-4-(3-(thiazol-2-yl-thio)-propylthio)2-pyridinyl]methyl]thio}-1H-benzimidazole By the procedure described in Example 1, the title compound (63% of theory) is obtained by reaction of 2-mercaptothiazole with 2-{[[4-(3-chloropropylthio)-3-methyl-2-pyridinyl]methyl]thio}-1H-benzimidazole and NaOH; colorless solid of melting point 121°–123° C.

10. 2-{[[3-Methyl-4-(3-(pyridin-2-yl-thio)-propylthio)-2-pyridinyl]methyl]thio}-1H-benzimidazole By the procedure described in Example 1, the title compound (87% of theory) is obtained by reaction of 2-mercaptopyridine with 2-{[[4-(3-chloropropylthio)-3-methyl-2-pyridinyl]methyl]thio}-1H-benzimidazole and NaOH; colorless solid of melting point 97°–99° C.

11. 2-{[[3-Methyl-4-(3-(pyrimidin-2-yl-thio)-propylthio)-2-pyridinyl]methyl]thio}-1H-benzimidazole By the procedure described in Example 1, the title compound is obtained as the monohydrate (92% of theory) by reaction of 2-mercaptopyrimidine with 2-{[[4-(3-chloropropylthio)-3-methyl-2-pyridinyl]methyl]thio}-1H-benzimidazole and NaOH; colorless solid of melting point 118°–119° C.

12. 2-{[[4-[(3-Benzimidazol-2-yl-thio)-propylthio-3-methyl-2-pyridinyl]methyl]thio}-1H-benzimidazole By the procedure described in Example 1, the title compound (62% of theory) is obtained by reaction of 2-mercaptobenzimidazole with 2-{[[4-(3-chloropropylthio)-3-methyl-2-pyridinyl]methyl]thio}-1H-benzimidazole and NaOH; colorless solid of melting point 177°–180° C. (decomposition).

13. 2-{[[3-Methyl-4-(3-(phenylthio-propylthio)-2-pryidinyl]methyl]thio}-1H-benzimidazole By the procedure described in Example 1, the title compound (95% of theory) is obtained by reaction of thiophenol 2-{[[4-(3-chloropropylthio)-3-methyl-2-pyridinyl]methyl]thio}-1H-benzimidazole and NaOH; colorless solid of melting point 141°–143° C.

14. 2-{[[3-Methyl-4-(3-(pyridine-1-oxo-2-yl-thio}-propylthio)-2-pyridinyl]methyl]thiol-1H-benzimidazole dihydrochloride By the procedure described in Example 1, the title compound is obtained as a viscous oil by reaction of 2-mercaptopyridine N-oxide with 2-{[[4-(3-chloropropylthio)-3-methyl-2-pyridinyl]methyl]thio}-1H- benzimidazole and NaOH. The product is extracted with methylene chloride, the extract is dried over potassium carbonate and evaporated to dryness, the residue is dissolved in isopropanol, 3 equivalents of concentrated hydrochloric acid are added and the mixture is heated to incipient distillation. The solid which has precipitated out is filtered off and dried in vacuo over KOH. The title compound (66% of theory) is obtained; colorless solid of melting point 71°–73° C. (decomposition).

15. 2-{[[3-Methyl-4-(2-(pyridine-2-yl-thio)-ethylthio)-2-pyridinyl]methyl]thio}-1H-benzimidazole By the procedure described in Example 1, the title compound (72% of theory) is obtained as a colorless solid of melting point 145°–147° C. by reaction of 2-mercaptopyridine with 2-{[[4-(2-chloroethylthio)-3-methyl-2-pyridinyl]methyl]thio}-1H-benzimidazole and sodium hydroxide solution followed by crystallization from isopropanol.

16. 2-{[[3-Methyl-4-[3-(4-methyl-pyrimidine-2-yl-thio)-propylthio]-2-pyridinyl]methyl]thio}-1H-benzimidazole By the procedure described in Example 1, the title compound is obtained by reaction of 2-mercapto-4-methylpyrimidine; beige solid, melting point 70°–72° C.; yield 77% of theory.

17. 2-{[[4-[3-(1-(2-Dimethylaminoethyl)-tetrazol-5-yl-thio)-propylthio)-3-methyl-2-pyridinyl]methyl]thio}-1H-benzimidazole trihydrochloride By the procedure described in Examples 14 and 1, the title compound is obtained by reaction with 1-(2-dimethylamino)-2-mercaptotetrazole; melting point 131°–133° C., decomposition; yield 40% of theory.

18. 2-{[[3-Methyl-4-(3-(1,3,4-thiadiazol-2-yl-thio)-propylthio)-2-pyridinyl]methyl]thio}-1H-benzimidazole trihydrochloride By the procedure described in Examples 14 and 1, the title compound is obtained by reaction with 2-mercapto-1,3,4-thiadiazole; melting point 167°–170° C., decomposition; yield 53% of theory.

19. 2-{[[3-Methyl-4-(3-(pyridin-4-yl-thio)-propylthio)-2-pyridinyl]methyl]thio}-1H-benzimidazole By the procedure described in Example 1, the title compound is obtained by reaction with 4-mercapto-pyridine; colorless powder; melting point: 164°–166° C.; yield 92% of theory.

20. 2-{[[3-Methoxy-4-(3-(1-methyl-tetrazol-5-yl-thio)-propylthio)-2-pyridinyl]methyl]thio}-1H-benzimidazole dihydrochloride By the procedure described in Examples 14 and 1, the title compound is obtained as colorless crystals by reaction of 2-{[[4-(3-chloropropylthio)-3-methoxy-2-pyridinyl]methyl]thio}-1H-benzimidazole with 1-methyl-5-mercaptotetrazole; melting point 135° C., decomposition; yield 84% of theory.

21. 2-{[[3-Methoxy-4-(3-(pyrimidin-2-yl-thio)-propylthio)-2-pyridinyl]methyl]thio}-1H-benzimidazole By the procedure described in Example 1, the title compound is obtained as a beige powder by reaction of 2-mercaptopyrimidine with 2-{[[4-(3-chloropropylthio)-3-methoxy-2-pyridinyl]methyl]thio}-1H-benzimidazole; melting point 88°–90° C., yield 77% of theory.

22. Sodium 5-(5-[2-(1H-benzimidazol-2-yl-thiomethyl)-3-methyl-4-pyridinyl]-1,5-dithiapent-1-yl}-tetrazole-1-acetate By the procedure described in Example 1, the title compound is obtained by reaction with 2-mercaptotetrazole-1-acetic acid and sodium hydroxide solution followed by precipitation with acetone and recrystallization from methanol/diisopropyl ether; beige powder; melting point from 180° C., decomposition; yield 34% of theory.

23. 2-{[[3-Methyl-4-(2-(1-methyl-tetrazol-5-yl-thio)-ethylthio)-2-pyridinyl]methyl]thio}-1H-benzimidazole By the procedure described in Example 1, the title compound (82% of theory) is obtained as a colorless solid by reaction of 1-methyl-5-mercaptotetrazole with 2-{[[4-(2-chloroethylthio)-3-methyl-2-pyridinyl]methyl]-thio)}-1H-benzimidazole and NaOH. Melting point 204°–208° C.

24. 2-{[[3-Methyl-4-(4-(1-methyl-tetrazol-5-yl-thio)-butylthio)-2-pyridinyl]methyl]thio}-1H-benzimidazole By the procedure described in Example 1, the title compound (48% of theory) is obtained as a colorless solid by reaction of 1-methyl-5-mercaptotetrazole with 2-{[[4-(4-chlorobutylthio)-3-methyl-2-pyridinyl]methyl]thio}-1H-benzimidazole and NaOH. Melting point 208°–210° C.

Starting Compounds

A1. 2-{[[4-(3-Chloropropylthio)-3-methyl-2-pyridinyl]methyl]thio}-1H-benzimidazole One equivalent of 2-chloromethyl-4-(3-chloropropylthio)-3-methylpyridine hydrochloride (dissolved in 10 ml of water) is added dropwise to a solution of 2-mercapto-1H-benzimidazole (1.5 g/10 mmol) in 40 ml of ethanol and 21 ml of 1N sodium hydroxide solution at 40° C. in the course of 20 min. The mixture is then stirred at 50°–60° C. for 2–3 hours and at room temperature for a further 3–4 hours, the ethanol is distilled off on a rotary evaporator (1 kPa/40° C.), the residue is extracted 3 times with 20 ml of methylene chloride each time and the extract is washed with 0.1N sodium hydroxide solution, dried over potassium carbonate and evaporated to dryness in vacuo. For purification, the crude product is chromatographed over silica gel (methylene chloride 20:1 to 3:1); the pure fractions collected are evaporated together in vacuo and the residue is crystallized from methylene chloride/diisopropyl ether. It is then recrystallized from methanol/toluene. Yield: 2.67 g (74%) of the title compound as a colorless solid of melting point 112°–114° C.

A2. 2-Chloromethyl-4-(3-chloropropylthio)-3-methylpyridine hydrochloride a) 2,3-Dimethyl-4-(3-hydroxypropylthio)pyridine N-oxide 6 g (60% pure) of NaOH are added in portions to 50 ml of dry N-methylpyrrolidone (NMP), the mixture is stirred for 15 min, 9.5 g (0.11 mol) of 3-hydroxypropyl mercaptan are metered in over a period of 20 min. and the mixture is stirred again for 30 min. until the evolution of gas has ended. A solution of 14.4 g (0.1 mol) of 4-chloro-2,3-dimethylpyridine N-oxide in 100 ml of NMP is then added dropwise in the course of 20 min. and the reaction mixture is stirred at room temperature for 1 hour, subsequently at 70° C. for 1 hour and thereafter at 100° C. for a further hour.

When the reaction has been terminated, the mixture is allowed to cool and is diluted with 500 ml of water and extracted 4 times with 300 ml of methylene chloride each time. The combined organic phases are washed with water, dried over magnesium sulfate and evaporated. The oily residue [10.0 g of crude 2,3-dimethyl-4-(3-hydroxypropylthio)-pyridine N-oxide] is employed directly in the subsequent stage.

b) 2-Hydroxymethyl-4-(3-hydroxypropylthio)-3-methylpyridine

The yellow oil obtained under a) is dissolved in 100 ml of acetic anhydride and the solution is stirred at 100° C. for 2 hours. After evaporation in vacuo, the brown oily residue is distilled in a bulb tube distillation apparatus and reacted further without purification.

The oily distillate is heated at the reflux temperature in 100 ml of 2N sodium hydroxide solution and 100 ml of isopropanol for 2 hours with stirring, isopropanol is distilled off, the residue is extracted 3 times with 100 ml of methylene chloride each time and the combined organic phases are washed with water, dried over potassium carbonate and concentrated in vacuo. 5.0 g of 2-hydroxymethyl-4-(3-hydroxypropylthio)-3-methylpyridine, which is reacted further without purification, are obtained.

c) 2-Chloromethyl-4-(3-chloropropylthio)-3-methylpyridine Hydrochloride 5.0 g of the oil from Example b) are dissolved in methylene chloride (100 ml), 4 equivalents of thionyl chloride are added dropwise and the mixture is stirred at room temperature for 20 hours. It is evaporated to dryness and 4.5 g of the title compound are obtained as an oily residue which gradually crystallizes and, if desired, can also be used as a solution in ethanol directly for the reaction with optionally substituted 2-mercaptobenzimidazoles.

B1. 2-{[[4-(2-Chloroethylthio)-3-methyl-2-pyridinyl]-methyl]thio}-1H-benzimidazole By the procedure described in Example A1., the title compound (62% of theory) is obtained as a colorless solid of melting point 178°–180° C. by reaction of 2-mercapto-1H-benzimidazole with 4-(2-chloroethylthio)-2-chloromethyl-3-methylpyridine hydrochloride and NaOH followed by crystallization from ethyl acetate.

B2. 4-(2-Chloroethylthio)-2-chloromethyl-3-methylpyridine Hydrochloride a) 2,3-Dimethyl-4-(2-hydroxyethylthio)pyridine N-oxide By the procedure described in Example A2.a), the title compound is obtained as an oily residue, which is employed in the subsequent stage without further purification, by reaction of 4-chloro-2,3-dimethylpyridine N-oxide with 2-mercaptoethanol and sodium hydride.

b) 4-(2-Hydroxyethylthio)-2-hydroxymethyl-3-methylpyridine

By the procedure described in Example A2.b), the title compound is obtained as an oily residue, which is employed in the subsequent stage without further purification, by reaction of the oil obtained under a) with acetic anhydride and subsequent hydrolysis with NaOH.

c) 4-(2-Chloroethylthio)-2-chloromethyl-3-methylpyridine Hydrochloride

By the procedure described in Example A2.c), the title compound is obtained as an oily residue, which is employed as a solution in ethanol directly for the reaction with 2-mercaptobenzimidazole, by reaction of the oil obtained under b) with thionyl chloride.

C1. 2-{[[4-(4-Chlorobutylthio)-3-methyl-2-pyridinyl]methyl]thio}-1H-benzimidazole By the procedure described in Example A1., the title compound (82% of theory) is obtained as a pale yellow solid of melting point 151°–153° C. by reaction of 2-mercapto-1H-benzimidazole with 4-(4-chlorobutylthio)-2-chloromethyl-3-methylpyridine hydrochloride and NaOH followed by crystallization from ethyl acetate/diisopropyl ether.

C2. 4-(4-Chlorobutylthio)-2-chloromethyl-3-methylpyridine Hydrochloride a) 2,3-Dimethyl-4-(4-hydroxybutylthio)pyridine N-oxide By the procedure described in Example A2.a), the title compound is obtained as an oily residue, which is employed in the subsequent stage without further purification, by reaction of 4-chloro-2,3-dimethylpyridine N-oxide with 4-mercaptobutanol and sodium hydride.

b) 4-(4-Hydroxybutylthio)-2-hydroxymethyl-3-methylpyridine

By the procedure described in Example A2.b), the title compound is obtained as an oily residue, which is employed in the subsequent stage without further purification, by reaction of the oil obtained under a) with acetic anhydride and subsequent hydrolysis with NaOH.

c) 4-(4-Chlorobutylthio)-2-chloromethyl-3-methylpyridine Hydrochloride

By the procedure described in Example A2.c), the title compound is obtained as an oily residue, which is employed as a solution in ethanol directly for the reaction with 2-mercaptobenzimidazole, by reaction of the oil obtained under b) with thionyl chloride.

D1. 2-{[[4-(3-Chloropropylthio)-3-methoxy-2-pyridinyl]-methyl]thio}-1H-benzimidazole Dihydrochloride 2-Mercapto-1H-benzimidazole (10 g) and 2-chloromethyl-4-(3-chloropropylthio)-3-methoxypyridine hydrochloride (1 equivalent) are stirred in 150 ml of isopropanol and 15 ml of water at 80° C. for 5 hours, the mixture is cooled and the solid which has precipitated out is filtered off and recrystallized from isopropanol/water. The title compound is obtained as a pale brown powder; melting point 117°–119° C. (decomposition); yield: 67% of theory.

D2. 2-Chloromethyl-4-(3-chloropropylthio)-3-methoxypyridine Hydrochloride

By the procedure described in Example A2 a, b, c, starting from 4-chloro-3-methoxy-2-methylpyridine N-oxide, the title compound is obtained as an oil which slowly crystallizes and is further reacted directly.

Commercial Utility

The excellent activity of compounds of the formula I and their salts against Helicobacter bacteria enables them to be used in human medicine as active compounds for the treatment of diseases caused by Helicobacter bacteria.

The invention therefore furthermore relates to a method for treatment of mammals, in particular humans, suffering from diseases caused by Helicobacter bacteria. The method comprises administering a therapeutically effective and pharmacologically tolerated amount of one or more compounds of formula I and/or of their pharmacologically tolerated salts to the sick individual.

The invention furthermore relates to compounds of formula I and their pharmacologically tolerated salts for use in the treatment of diseases caused by Helicobacter bacteria.

The invention also relates to the use of compounds of formula I and their pharmacologically tolerated salts in the preparation of medicaments which are employed for treatment of diseases caused by Helicobacter bacteria.

The invention furthermore relates to medicaments for combating Helicobacter bacteria which comprise one or more compounds of formula I and/or their pharmacologically tolerated salts.

Of the Helicobacter strains against which the compounds of the formula I have proven active, the strain Helicobacter pylori may be mentioned in particular.

The medicaments are prepared by methods which are known per se and are familiar to the expert. As medicaments, the pharmacologically active compounds of the formula I and their salts (=active compounds) are employed either as such or, preferably, in combination with suitable pharmaceutical auxiliaries, for example in the form of tablets, coated tablets, capsules, emulsions, suspensions, gels or solutions, the active compound content advantageously being between 0.1 and 95%.

The auxiliaries which are suitable for the desired medicament formulations are familiar to the expert on the basis of his expert knowledge. In addition to solvents, gel-forming agents, tableting auxiliaries and other active compound excipients, it is possible to use, for example, antioxidants, dispersing agents, emulsifiers, antifoams, flavor correctants, preservatives, solubilizing agents, dyestuffs or permeation promoters and complexing agents (for example cyclodextrins).

The active compounds can be administered, for example, parenterally (for example intravenously) or, in particular, orally.

In human medicine, the active compounds are in general administered in a daily dose of about 0.2 to 50, preferably 1 to 30 mg/kg of body weight, if appropriate in the form of several, preferably 2 to 6, individual doses in order to achieve the desired result.

In this connection, an aspect which is essential to the invention and should be mentioned in particular is that the compounds of the formula I in which n is the number 0 prove to be active against Helicobacter bacteria even when the doses administered are below the doses which it would be necessary to employ to achieve an inhibition of secretion of gastric acid sufficient for therapeutic purposes.

Compounds of formula I in which n is the number 1 also have—in addition to their activity against Helicobacter bacteria—a pronounced inhibiting action on secretion of gastric acid. These compounds can accordingly also be employed for the treatment of diseases caused by increased secretion of gastric acid.

The compounds according to the invention can also be administered in fixed or free combination together with a substance which neutralizes gastric acid and/or inhibits secretion of gastric acid and/or with a substance suitable for conventional control of Helicobacter pylori.

Examples which may be mentioned of substances which neutralize gastric acid are sodium bicarbonate or other antacids (such as aluminum hydroxide, magnesium aluminate or magaldrate). Examples which may be mentioned of substances which inhibit secretion of gastric acid are $H_2$ blockers (for example cimetidine and ranitidine), $H^+/K^+$-ATPase inhibitors (for example lansoprazol, omeprazol or, in particular, pantoprazol), and so-called peripheral anticholinergics (for example pirenzepine and telenzepine).

Substances which are suitable for conventional control of Helicobacter pylori and which may be mentioned in particular are antimicrobially active substances, such as, for example, penicillin G, gentamicin, erythromycin, nitrofurazone, tinidazole, nitrofurantoin, furazolidone, metronidazole and, in particular, amoxycillin, but also bismuth salts, such as, for example, bismuth citrate.

Biological Studies

The compounds of formula I have been investigated in respect of their activity against Helicobacter pylori in accordance with the method described by Tomoyuki Iwahi et al. (Antimicrobial Agents and Chemo-therapy, 1991, 490–496) using Columbia agar (Oxoid) over a growth period of 4 days. The approximate MIC 50 values listed in the following Table 2 resulted from these tests for the compounds studied (the numbers stated for the compounds agree with the compound numbers in the description).

TABLE 2

| Compound No. | Approx. MIC 50 value ($\mu$g/ml) |
| --- | --- |
| 1 | 0.1 |
| 2 | 0.05 |
| 3 | 0.05 |
| 5 | 0.5 |
| 6 | 0.1 |
| 8 | 0.05 |
| 9 | 0.05 |
| 10 | 0.05 |
| 11 | 0.05 |
| 12 | 0.05 |
| 13 | 0.05 |
| 16 | 0.05 |
| 18 | 0.05 |
| 19 | 0.05 |
| 24 | 0.05 |

I claim:

1. A compound of formula I

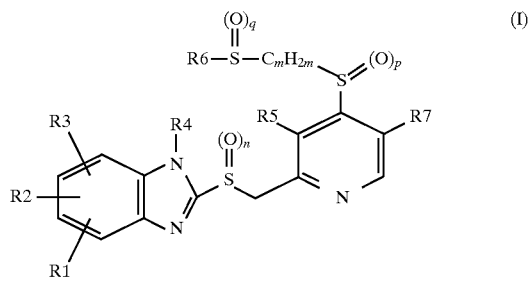

in which

R1 is hydrogen, 1-4C-alkyl or 1-4C-alkoxy,

R2 is hydrogen, 1-4C-alkyl, 1-4C-alkoxy, halogen, trifluoromethyl, 1-4C-alkoxy which is completely or predominantly substituted by fluorine, or chlorodifluoromethoxy or 2-chloro-1,1,2-trifluoroethoxy, or, together with R3, bonded to adjacent ring carbons, is 1-2C-alkylenedioxy which, optionally, is completely or partly substituted by fluorine, or chlorotrifluoroethylenedioxy, R3 is hydrogen, 1-4C-alkoxy which is completely or predominantly substituted by fluorine, or chlorodifluoromethoxy or 2-chloro-1,1,2-trifluoroethoxy or, together with R2, bonded to adjacent ring carbons, is 1-2C-alkylenedioxy which, optionally, is completely or partly substituted by fluorine, or chlorotrifluoroethylenedioxy, R4 is hydrogen or 1-4C-alkyl, R5 is hydrogen, 1-4C-alkyl or 1-4C-alkoxy, R6 is a cyclic or bicyclic radical which is substituted by R8 and R9 and is a member selected from the group consisting of benzene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine N-oxide, pyrimidine and benzimidazole, R7 is hydrogen, 1-4C-alkyl or 1-4C-alkoxy, R8 is hydrogen, 1-4C-alkyl, hydroxyl, 1-4C-alkoxy, halogen, nitro, carboxyl, 1-4C-alkoxycarbonyl, guanidino, 1-4C-alkyl which is substituted by R10, or —N(R11)R12, R9 is hydrogen, 1-4C-alkyl, 1-4C-alkoxy, fluorine or trifluoromethyl, R10 is hydroxyl, 1-4C-alkoxy, carboxyl, 1-4C-alkoxycarbonyl or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino or morpholino radical, R13 is hydrogen, 1-4C-alkyl or 1-4C-alkoxy, m is a number from 2 to 7, n is the number 0 or 1, p is the number 0 or 1 and q is the number 0 or 1, or a salt thereof.

2. A compound of the formula I as claimed in claim 1, in which

R1 is hydrogen, 1-4C-alkyl or 1-4C-alkoxy,

R2 is hydrogen, 1-4C-alkyl, 1-4C-alkoxy, halogen, trifluoromethyl, 1-4C-alkoxy which is completely or predominantly substituted by fluorine, or chlorodifluoromethoxy or 2-chloro-1,1,2-trifluoroethoxy, or, together with R3, is 1-2C-alkylenedioxy which, optionally, is completely or partly substituted by fluorine, or chlorotrifluoroethylenedioxy, R3 is hydrogen, 1-4C-alkoxy which is completely or predominantly substituted by fluorine, or chlorodifluoromethoxy or 2-chloro-1,1,2-trifluoroethoxy, or, together with R2, is 1-2C-alkylenedioxy which, optionally, is completely or partly substituted by fluorine, or chlorotrifluoroethylenedioxy, R4 is hydrogen or 1-4C-alkyl, R5 is hydrogen, 1-4C-alkyl or 1-4C-alkoxy, R6 is a cyclic or bicyclic radical which is substituted by R8 and R9 and is a member selected from the group consisting of benzene, furan, thiophene, pyrrole, oxazole, isoxazole, thiazole, thiazoline, isothiazole, imidazole, imidazoline, pyrazole, triazole, tetrazole, thiadiazole, oxadiazole, pyridine, pyridine N-oxide, pyrimidine and benzimidazole, R7 is hydrogen, 1-4C-alkyl or 1-4C-alkoxy, R8 is hydrogen, 1-4C-alkyl, hydroxyl, 1-4C-alkoxy, halogen, guanidino, 1-4C-alkyl which is substituted by R10, or —N(R11)R12, R9 is hydrogen, 1-4C-alkyl, 1-4C-alkoxy, fluorine or trifluoromethyl, R10 is hydroxyl, 1-4C-alkoxy, carboxyl, or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino or morpholino radical, R13 is hydrogen, 1-4C-alkyl or 1-4C-alkoxy, m is a number from 2 to 7, n is the number 0 or 1, p is the number 0 or 1 and q is the number 0 or 1, or a salt thereof.

3. A compound of the formula I as claimed in claim 1, in which R8 is nitro, carboxyl or 1-4C-alkoxycarbonyl, and/or in which R10 is 1-4C alkoxycarbonyl, or a salt thereof.

4. A compound of the formula I as claimed in claim 1, in which

R1 is hydrogen,

R2 is hydrogen, halogen, methoxy, difluoromethoxy or trifluoromethyl,

R3 is hydrogen,

R4 is hydrogen,

R5 is hydrogen, 1-4C-alkyl or 1-4C-alkoxy,

R6 is a cyclic radical which is substituted by R8 and R9 and is a member selected from the group consisting of benzene, isoxazole, thiazole, imidazole, triazole, tetrazole, thiadiazole, pyridine, pyridine N-oxide, and pyrimidine R7 is hydrogen or 1-4C-alkyl, R8 is hydrogen, 1-4C-alkyl, 1-4C-alkyl which is substituted by R10, or amino, R9 is hydrogen or 1-4C-alkyl, R10 is hydroxyl, carboxyl or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino radical, R13 is hydrogen, 1-4C-alkyl or 1-4C-alkoxy, m is a number from 2 to 4, n is the number 0 or 1, p is the number 0 and q is the number 0, or a salt thereof.

5. A compound of the formula I as claimed in claim 1, in which

R1 is hydrogen,

R2 is hydrogen, halogen or methoxy,

R3 is hydrogen,

R4 is hydrogen,

R5 is hydrogen, 1-4C-alkyl or 1-4C-alkoxy,

R6 is a cyclic radical which is substituted by R8 and R9 and is a member selected from the group consisting of benzene, isoxazole, thiazole, imidazole, triazole, tetrazole, thiadiazole, pyridine, pyridine N-oxide, pyrimidine and benzimidazole, R7 is hydrogen or 1-4C-alkyl, R8 is hydrogen, 1-4C-alkyl, hydroxyl, nitro, guanidino, carboxyl, 1-4C-alkoxycarbonyl, 1-4C-alkyl which is substituted by R10, or amino, R9 is hydrogen or 1-4C-alkyl, R10 is hydroxyl, carboxyl, 1-4C-alkoxycarbonyl or —N(R11)R12, in which R11 is hydrogen, 1-4C-alkyl or —CO—R13 and R12 is hydrogen or 1-4C-alkyl, or in which R11 and R12, together and including the nitrogen atom to which they are both bonded, are a piperidino radical, R13 is hydrogen, 1-4C-alkyl or 1-4C-alkoxy, m is a number from 2 to 4, n is the number 0 or 1, p is the number 0 and q is the number 0, or a salt thereof.

6. A compound of the formula I as claimed in claim 1, in which

R1 is hydrogen,

R2 is hydrogen or methoxy,

R3 is hydrogen,

R4 is hydrogen,

R5 is 1-4C-alkyl or 1-4C-alkoxy,

R6 is a cyclic radical which is substituted by R8 and R9 and is a member selected from the group consisting of benzene, thiazole, triazole, tetrazole, thiadiazole and pyridine, R7 is hydrogen, R8 is hydrogen, 1-4C-alkyl, or methyl or ethyl which is substituted by R10, R9 is hydrogen or 1-4C-alkyl, R10 is hydroxyl, carboxyl or —N(R11)R12, in which R11 is 1-4C-alkyl and R12 is 1-4C-alkyl, or in which R11 and R12, together and including the nitrogen atom to which they are both bonded, are a piperidino radical, m is the number 2 or 3, n is the number 0, p is the number 0 and q is the number 0, or a salt thereof.

7. A compound of the formula I as claimed in claim 1, in which

R1 is hydrogen,

R2 is hydrogen, fluorine or methoxy,

R3 is hydrogen,

R4 is hydrogen,

R5 is 1-4C-alkyl or 1-4C-alkoxy,

R6 is a cyclic radical which is substituted by R8 and R9 and is a member selected from the group consisting of benzene, thiazole, imidazole, triazole, tetrazole, thiadiazole, pyridine, pyrimidine and benzimidazole, R7 is hydrogen, R8 is hydrogen, 1-4C-alkyl, hydroxyl, nitro, guanidino, carboxyl, 1-4C-alkoxycarbonyl, or methyl or ethyl which is substituted by R10, R9 is hydrogen or 1-4C-alkyl, R10 is hydroxyl, carboxyl or —N(R11)R12, in which R11 is 1-4C-alkyl and R12 is 1-4C-alkyl, or in which R11 and R12, together and including the nitrogen atom to which they are both bonded, are a piperidino radical, m is a number from 2 to 4, n is the number 0, p is the number 0 and q is the number 0, or a salt thereof.

8. A compound of the formula I as claimed in claim 1, in which

R1 is hydrogen,

R2 is hydrogen,

R3 is hydrogen,

R4 is hydrogen,

R5 is 1-4C-alkyl or 1-4C-alkoxy,

R6 is a cyclic radical which is substituted by R8 and R9 and is a member selected from the group consisting of benzene, thiazole, triazole, tetrazole, thiadiazole and pyridine, R7 is hydrogen, R8 is hydrogen, methyl, or methyl or ethyl which is substituted by R10, R9 is hydrogen, R10 is hydroxyl, carboxyl or —N(R11)R12, in which R11 is methyl and R12 is methyl, or in which R11 and R12, together and including the nitrogen atom to which they are both bonded, are a piperidino radical, m is the number 2 or 3, n is the number 0, p is the number 0 and q is the number 0, or a salt thereof.

9. A compound of the formula I as claimed in claim 1, in which

R1 is hydrogen,

R2 is hydrogen or fluorine,

R3 is hydrogen,

R4 is hydrogen,

R5 is 1-4C-alkyl or 1-4C-alkoxy,

R6 is a cyclic radical which is substituted by R8 and R9 and is a member selected from the group consisting of benzene, thiazole, imidazole, triazole, tetrazole, thiadiazole, pyridine, pyrimidine and benzimidazole, R7 is hydrogen, R8 is hydrogen, methyl, nitro, 1-4C-alkoxycarbonyl, or methyl or ethyl which is substituted by R10, R9 is hydrogen, R10 is hydroxyl, carboxyl or —N(R11)R12, in which R11 is methyl and R12 is methyl, or in which R11 and R12, together and including the nitrogen atom to which they are both bonded, are a piperidino radical, m is a number from 2 to 4, n is the number 0, p is the number 0 and q is the number 0, or a salt thereof.

10. A compound of the formula I as claimed in claim 1, in which

R1 is hydrogen,

R2 is hydrogen,

R3 is hydrogen,

R4 is hydrogen,

R5 is 1-4C-alkyl or 1-4C-alkoxy,

R6 is a cyclic radical which is substituted by R8 and R9 and is a member selected from the group consisting of benzene, thiazole, imidazole, triazole, tetrazole, thiadiazole, pyridine and pyrimidine, R7 is hydrogen, R8 is hydrogen, methyl, or methyl or ethyl which is substituted by R10, R9 is hydrogen, R10 is carboxyl or —N(R11)R12, in which R11 is methyl and R12 is methyl, m is a number from 2 to 4, n is the number 0, p is the number 0 and q is the number 0, or a salt thereof.

11. A compound of claim 1 wherein R2 and R3 are bonded at the 5- and 6-positions of the benzo part of the benzimidazole ring and, together, are 1-2C-alkylenedioxy which, optionally, is completely or partly substituted by fluorine, or chlorotrifluoroethylenedioxy.

12. A compound of claim 1 wherein R2 is hydrogen, 1-4C-alkyl, 1-4C-alkoxy, halogen, trifluoromethyl, 1-4C-alkoxy which is completely or predominately substituted by fluorine, or chlorodifluoromethoxy or 2-chloro-1,1,2-trifluoroethoxy.

13. A process for the preparation of a compound of the formula I as claimed in claim 1, in which R1, R2, R3, R4, R5, R6, R7, m, n, p and q have the meanings given in claim 1, or of one of its salts, which comprises reacting a mercaptobenzimidazole of formula II

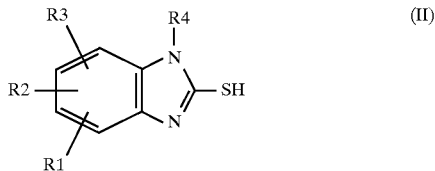

in which R1, R2, R3 and R4 have the meanings given in claim 1, with a picoline derivative III

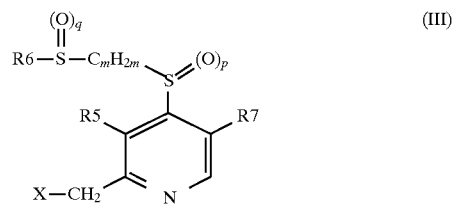

in which R5, R6, R7, m, p and q have the meanings given in claim 1 and X is a suitable leaving group.

14. A medicament composition comprising a suitable carrier and a compound of formula I as claimed in claim 1 or a pharmacologically tolerated salt thereof.

15. A method of treating a mammal afflicted with a condition caused by Helicobacter bacteria which comprises administering to the mammal an effective amount of a compound of formula I as claimed in claim 1 or one of its pharmacologically-tolerated salts.

16. In compounding a medicament composition having an effective amount of an active component for combating Helicobacter bacteria, the improvement wherein the active component is a compound of formula I as claimed in claim 1 or one of its pharmacologically-tolerated salts.

* * * * *